(12) United States Patent
Mackenzie

(10) Patent No.: US 10,022,246 B2
(45) Date of Patent: Jul. 17, 2018

(54) INTERLAMINAR FIXATION DEVICE

(71) Applicant: Donald Mackenzie, McKinney, TX (US)

(72) Inventor: Donald Mackenzie, McKinney, TX (US)

(*) Notice: Subject to any disclaimer, the term of this patent is extended or adjusted under 35 U.S.C. 154(b) by 0 days.

(21) Appl. No.: 14/972,064

(22) Filed: Dec. 16, 2015

(65) Prior Publication Data

US 2016/0166407 A1 Jun. 16, 2016

Related U.S. Application Data

(60) Provisional application No. 62/092,640, filed on Dec. 16, 2014, provisional application No. 62/268,258, filed on Dec. 16, 2015.

(51) Int. Cl.
| | |
|---|---|
| *A61B 17/70* | (2006.01) |
| *A61F 2/46* | (2006.01) |
| *A61B 17/16* | (2006.01) |
| *A61F 2/44* | (2006.01) |
| *A61F 2/30* | (2006.01) |

(52) U.S. Cl.
CPC ........ *A61F 2/4611* (2013.01); *A61B 17/1604* (2013.01); *A61B 17/7062* (2013.01); *A61F 2/44* (2013.01); *A61F 2/442* (2013.01); *A61F 2/4684* (2013.01); *A61F 2002/30261* (2013.01); *A61F 2002/30515* (2013.01); *A61F 2002/30579* (2013.01); *A61F 2002/30892* (2013.01); *A61F 2002/4622* (2013.01)

(58) Field of Classification Search
CPC .... A61B 17/7065–17/7068; A61F 2/44; A61F 2/447; A61F 2/4611
See application file for complete search history.

(56) References Cited

U.S. PATENT DOCUMENTS

| | | | |
|---|---|---|---|
| 5,800,550 A * | 9/1998 | Sertich | A61F 2/447 606/247 |
| 7,879,104 B2 | 2/2011 | Dewey et al. | |
| 8,062,374 B2 * | 11/2011 | Markworth | A61F 2/447 623/17.11 |
| 8,105,358 B2 | 1/2012 | Phan | |
| 8,114,131 B2 | 2/2012 | Kohm et al. | |

(Continued)

*Primary Examiner* — Eduardo C Robert
*Assistant Examiner* — Michelle C Eckman
(74) *Attorney, Agent, or Firm* — John G. Fischer, Esq.; Scheef & Stone, L.L.P.

(57) ABSTRACT

An interlaminar fixation device ("ILFD") and related tools for implanting and extracting the ILFD in surgical procedures to provide support for patients having degenerative spinal conditions. The ILFD comprises an implant body, a pair of fixation pin assemblies, and a locking plug. The body may be a boxlike structure made of a material such as polyetheretherketone (PEEK) or other material with similar beneficial properties. An implant-sizing tool is provided for determining the appropriately sized ILFD. An implant-grasper tool is provided for grasping the ILFD for insertion and positioning of the ILFD. A bone-punch tool is provided for creating openings aligned for insertion of fixation pins. A pin-inserter tool is provided for urging fixation pins into position. A locking-plug inserter tool is provided for inserting the locking plug into the body of the ILFD. A locking-plug extractor tool is provided for removing the locking plug.

22 Claims, 55 Drawing Sheets

(56) References Cited

U.S. PATENT DOCUMENTS

| | | |
|---|---|---|
| 8,157,842 B2 | 4/2012 | Phan et al. |
| 8,394,145 B2 | 3/2013 | Weiman |
| 8,518,083 B2 | 8/2013 | Yue |
| 2005/0033429 A1* | 2/2005 | Kuo .................. A61F 2/447 623/17.11 |
| 2005/0049590 A1* | 3/2005 | Alleyne ............ A61F 2/442 623/17.11 |
| 2006/0106397 A1* | 5/2006 | Lins .............. A61B 17/7065 606/90 |
| 2009/0054988 A1 | 2/2009 | Hess |
| 2009/0234389 A1 | 9/2009 | Chuang et al. |
| 2012/0232663 A1 | 9/2012 | Zipnick |
| 2015/0045893 A1* | 2/2015 | Dinville ............ A61F 2/44 623/17.16 |

\* cited by examiner

INTERLAMINAR FIXATION DEVICE

CROSS-REFERENCE TO RELATED APPLICATIONS

This application claims the benefit of U.S. Provisional Application Nos. 62/092,640 and 62/268,285, filed on Dec. 16, 2014 and Dec. 16, 2015, respectively.

FIELD OF THE INVENTION

The present invention is directed to an interlaminar fixation device of the type used in surgical procedures to provide support for patients having degenerative spinal conditions.

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

The treatment of degenerative lumbar spinal stenosis is conventionally treated by wide laminectomy and decompression of the spinal canal with or without spinal fusion. Spinal fusion, when required because of destabilization from the decompression, is usually associated with internal fixation making it a major procedure with significant morbidity to the patient.

Degenerative lumbar spinal stenosis causes neurological symptoms in the lower extremities and/or back pain. The symptoms may be constant with variations in intensity, depending upon position and activity, or may be intermittent and brought on by certain activities, particularly walking and standing.

The positional nature of the symptoms may be due to instability but most often is due to the fact that the normal posture of the lumbar spine is one of lordosis, which decreases the cross-sectional area of the spine. When the patient is sitting, lordosis decreases, increasing the cross-sectional area and relieving the symptoms.

Interspinous mechanical blocking devices, such as X-Stop by Medtronic, are commercially available. Such devices are pushed through the interspinous ligament and work by blocking extension of the spine. Unfortunately, such device has a very high failure rate, largely because the spinous process is the weakest part of the vertebra, but also because the population demographics of people requiring this type of operation are such that many of them suffer from osteoporosis.

Recently, another device, Coflex® by Paradigm Spine, LLC, was commercially released in the United States. This device is inserted by resecting the interspinous ligament and some of the inferior edge of the superior spinous process at the level which the device is to be inserted. Flanges at each end of the device can be pressed down so that they grasp the spinous process above and below. The flanges also contain holes through which small screws can be inserted.

This device also has a relatively high failure rate. The device has a fairly large diameter curve to make insertion of the device easier. This design results in forces which contain a vector attempting to displace the device back outwards from its position in the spine. If no securing screws have been placed, the device tends to dislocate posteriorly, resulting in a return of symptoms. If one screw is used, the device tends to pivot around that screw as it dislocates posteriorly, resulting in the same return of symptoms due to failure to prevent increased lumbar lordosis. When two screws are used, particularly where there is osteoporosis in the spinous process, the spinous process may fracture through the screw hole(s), resulting in posterior displacement.

Accordingly, there is a need for a blocking device for alleviating back pain. There is a need for such a blocking device to be easily inserted with a smaller incision than with insertion of conventional devices. There is further a need for such a blocking device to remain in place. There is still further a need for such a blocking device to be capable of extraction. There is a still further a need for tooling for easily inserting and extracting such a blocking device.

SUMMARY OF THE INVENTION

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

The present invention provides an interlaminar fixation device ("the ILFD") and insertion tools. The ILFD is inserted into the back of the spine to prevent a patient from bending too far backward at the narrowed segment, a position that for patients with spinal stenosis can cause leg pain (sciatica) and/or lower back pain. The ILFD is designed to avoid or at least significantly reduce the effect of posteriorly dislocating vector forces acting upon the implant. It is an almost boxlike construct with small radii on the corners. It is fixed with pins that engage the spinous processes in the sagittal plane and which do not restrict motion in flexion, only blocking extension. The surgical incision required to implant the ILFD is significantly less than of that required to insert conventional devices. Additionally, conventional devices require transversal bolt insertions which have several disadvantages. Insertion of the ILFD requires less muscular dissection which results in less physical invasion, faster healing, less pain, and lower risk of infection. An additional advantage of the present invention is that it requires less penetration of the colidal surface of the spinal process, and does not require grasping the spinal process to insert, thus lowering the risk of damage on insertion. The ILFD of the present invention is designed to be used in combination with removal of the ligamentum flavum, which further assists in decompressing the spine.

The ILFD comprises four components: an implant body, a pair of fixation pin assemblies (or spike strips), and a locking plug. The body may be a boxlike structure made of a material such as polyetheretherketone (PEEK) or other material with similar beneficial properties.

The ILFD may be produced in multiple sizes to accommodate the difference in the size of the patients. Titanium or tantalum rods may be embedded in the plastic so that the position of the ILFD can be assessed radiologically. The spike strips may be made of a titanium alloy. The strip may have a square section and have, at a distance from the inserted end, a breakoff notch. Between the inserted end and the notch, there are two cephalad spikes and two caudad spikes. The tips of the spikes are preferably oval.

The plug may be made of either PEEK or titanium or similar material. There is either a single threaded hole or dual clean holes for engagement of a plug-inserter tool at the dorsal surface. The ventral surface of the plug may be rounded for easier insertion into the implant body. There is a small ridge ventral to the dorsal surface which engages a notch on the inside of the body and thus prevents backing out. The notch may be present on only one side, but there may be two grooves on the inside of the body, one on the left and one on the right, so that the plug can be inserted without reference to the orientation of the ridge. In yet another embodiment, the plug has a orientation slot.

The present invention provides tooling. An implant-sizing tool is provided for determining the appropriately sized ILFD. An implant-grasper tool is provided for grasping the ILFD for insertion and positioning of the ILFD. A bone-punch tool is provided for creating openings aligned for insertion of fixation pins. A pin-inserter tool is provided for urging fixation pins into position. A locking-plug inserter tool is provided for inserting the locking plug into the body of the ILFD. A locking-plug extractor toll is also provided for removing the locking plug.

Various refinements of the features noted above may exist in relation to various aspects of the present embodiments. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of the embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not require any particular orientation of the components. The terms "helical" and "spiral" are not intended to require perfectly mathematical helix or spirals, and are particularly intended to include square ended, closed ended, and ground versions of springs of these types, and also as the channels that would receive any of these shapes.

Figure 1:
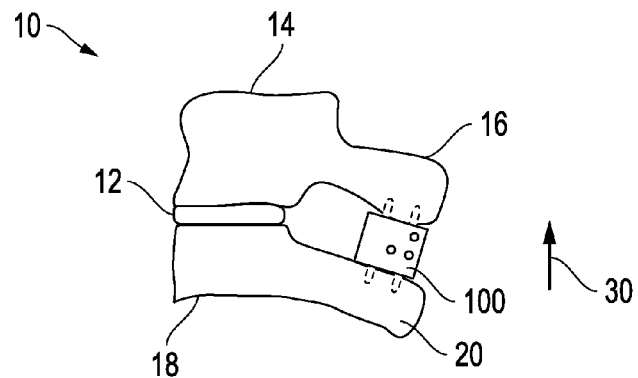
FIG. 1 depicts a side view of an embodiment of an interlaminar fixation device ("ILFD") exemplified after implantation in a spine.

Turning to FIG. 1, a side view of interlaminar fixation device ("ILFD") 100 is exemplified having been implanted in spine 10 (only two vertebrae shown) of a patient. Spine 10 is oriented as shown by arrow 30, wherein arrow 30 points cephalad (towards the head of the patient). Spine 10 comprises cephalad vertebra 14 having cephalad spinous process 16 and caudal vertebra 18 having caudal spinous process 20. Disc 12 is located between the cephalad and caudal vertebrae 14 and 18 as shown. Supra spinous ligament, ligament flavum, interspinous ligament, etc. of spine 10 have been omitted for clarity. ILFD 100 is shown implanted between cephalad spinous process 16 and caudal spinous process 20 using the tooling and procedures described herein.

Figure 2:
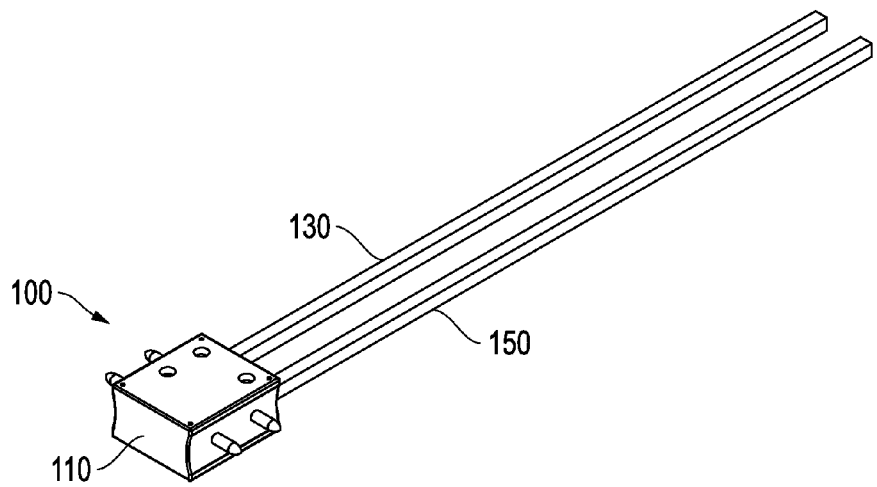
FIG. 2 depicts an isometric view of the ILFD of FIG. 1 exemplified as fully assembled.
Figure 3:
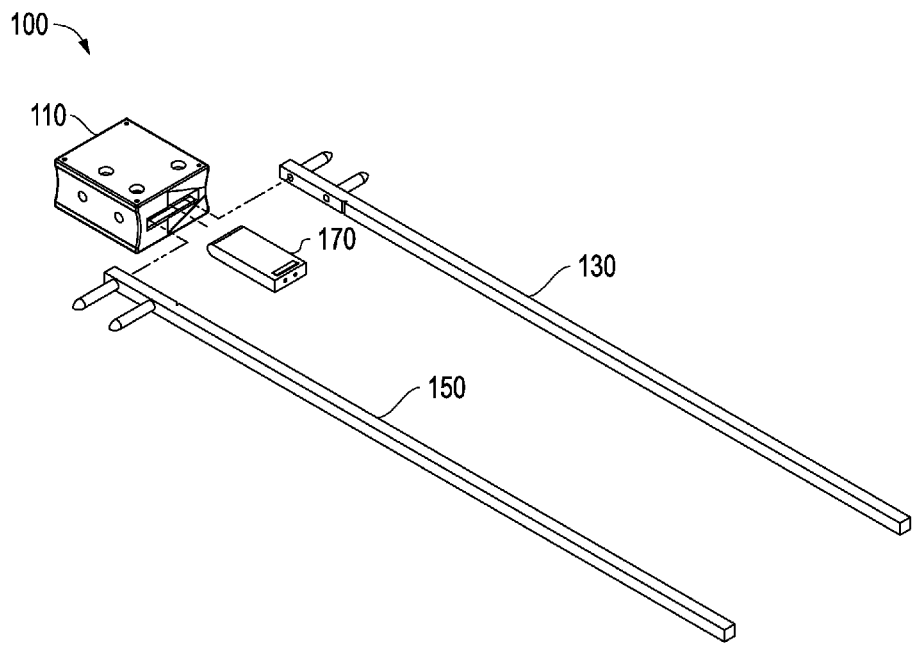
FIG. 3 depicts an exploded view of the ILFD of FIG. 2.
Figure 4:
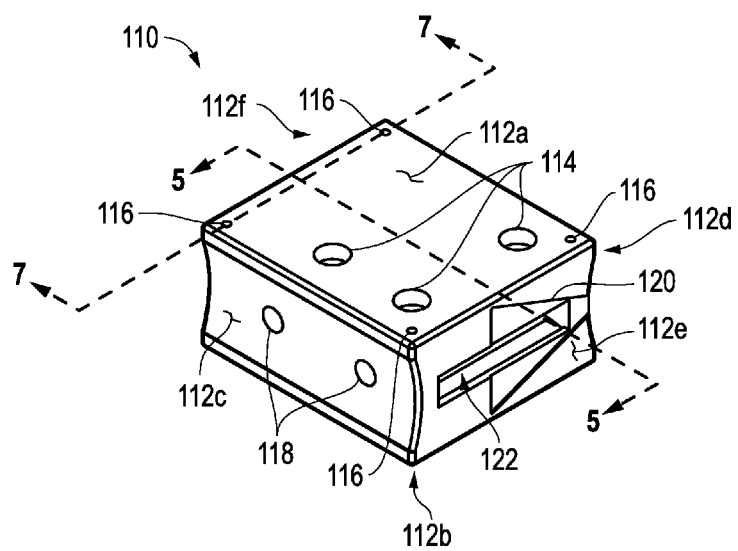
FIG. 4 depicts an isometric view of the implant body of the ILFD of FIG. 2.
Figure 5:
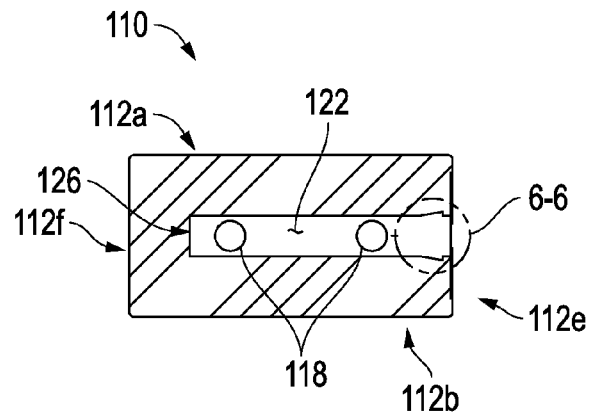
FIG. 5 depicts a cross-sectional view of the implant body of FIG. 4 taken along section line 5-5.
Figure 6:
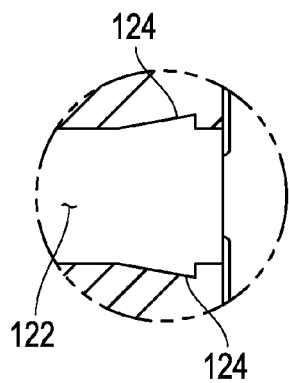
FIG. 6 depicts a close-up view of the implant body of FIG. 4 taken along line 6-6.
Figure 7:
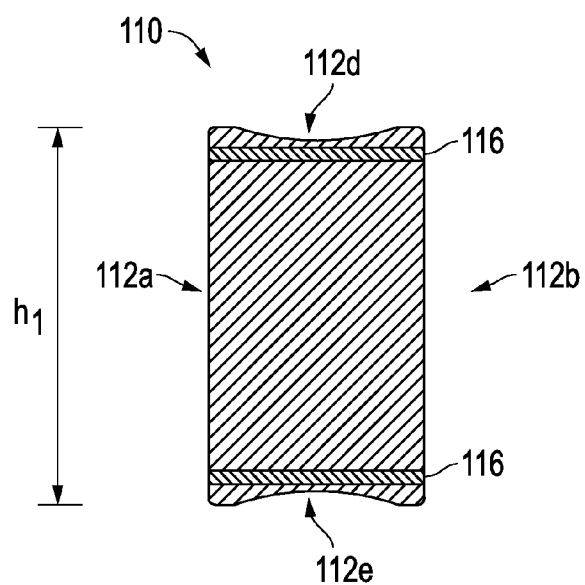
FIG. 7 depicts a cross-sectional view of the implant body of FIG. 4 taken along section line 7-7.

Referring to FIGS. 2-3, ILFD 100 is exemplified in fully assembled form prior to detachment of breakaway portions (discussed below) of cephalad fixation-pin assembly 130 and caudal fixation-pin assembly 150. ILFD 100 comprises implant body 110, cephalad fixation-pin assembly 130, caudal fixation-pin assembly 150, and locking plug 170 (or alternatively locking plug 900).

Referring to FIGS. 4-7, implant body 110 is shown in more detail. Implant body 110, preferably fabricated from polyetheretherketone (PEEK), has: left surface 112a and an opposite right surface 112b; caudal surface 112c and an opposite cephalad surface 112d; and dorsal surface 112e and an opposite ventral surface 112f. Orientation indicator 120 is provided on dorsal surface 112e to indicate visually proper orientation during implantation. Notches 114 are provided through left surface 112a and similarly on right surface 112b (not shown). Placement-detection rods 116 are provided as shown and are preferably tantalum rods or another material, such as titanium, that can be radiologically assessed. Fixation-pin openings 118 are provided through caudal surface 112c and similarly through cephalad surface 112d (not shown). Slot 122 is provided through dorsal surface 112e and is configured for receiving cephalad fixation-pin assembly 130, caudal fixation-pin assembly 150, and locking plug 170. Implant body 110 has height $h_1$. Preferably, implant bodies of various sizes will be on hand during implantation procedure and one of appropriate size for the patient is selected. Preferably, implant body 110 has two versions, one with height $h_1$ equal to 14 mm and the other with height $h_1$ equal to 16 mm. Preferably, implant body 110 has a depth (from dorsal surface 112e to ventral surface 112f) equal to 16 mm and a width (from left surface 112a to right surface 112b) equal to 8 mm.

Figure 8:
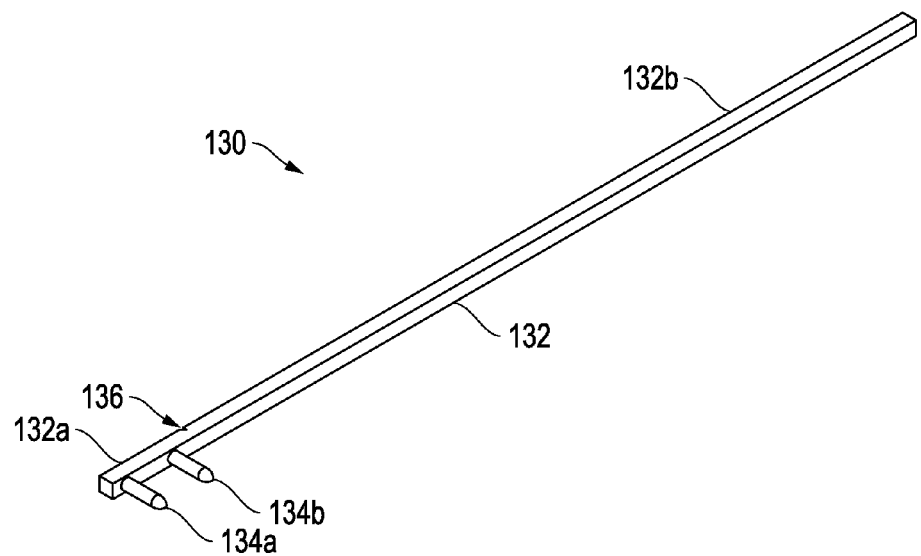
FIG. 8 depicts an isometric view of a cephalad fixation-pin assembly of the ILFD of FIG. 2.
Figure 9:
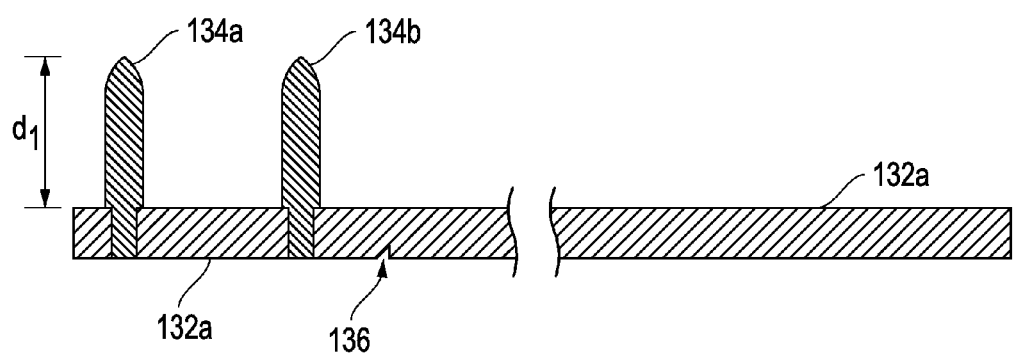
FIG. 9 depicts a cross-sectional view of the cephalad fixation-pin assembly of FIG. 8.

Referring to FIGS. 8-9, cephalad fixation-pin assembly 130 is provided. Fixation-pin 130 comprises rod 132 and cephalad fixation pins 134a and 134b. Rod 132 has embedded portion 132a and breakaway portion 132b, which are separated by breakaway notch 136. Fixation pins 134a and 134b have a depth $d_1$, which is preferably equal to 6 mm, and are preferably 1.5 mm in diameter at their base. Rod 132 preferably has a 2 mm×2 mm square cross section. Fixation pins 134a and 134b have tips or ends that are ogival as shown. Preferably, rod 132 and fixation pins 134a and 134b are fabricated from Tivanium®, however other suitable materials may be used.

Figure 10:
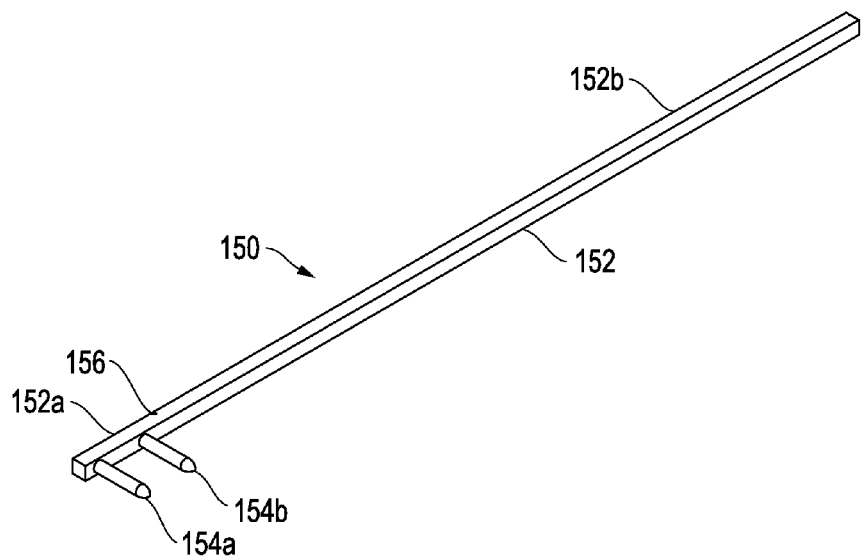
FIG. 10 depicts an isometric view of a caudal fixation-pin assembly of the ILFD of FIG. 2.
Figure 11:
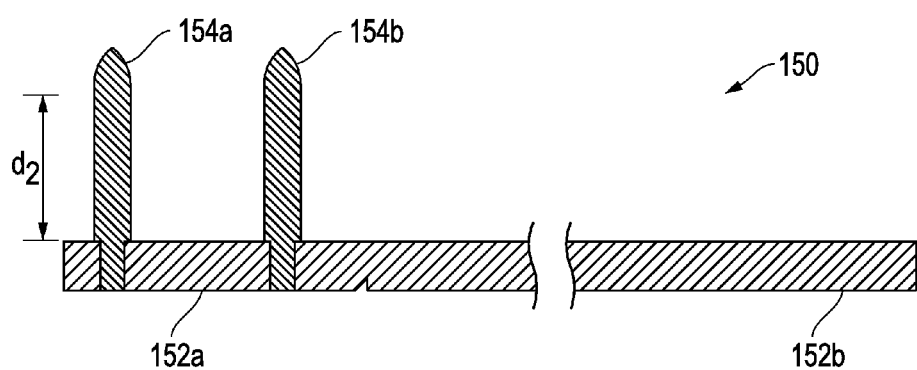
FIG. 11 depicts a cross-sectional view of the caudal fixation-pin assembly of FIG. 10.

Referring to FIGS. 10-11, caudal fixation-pin assembly 150 is provided. Fixation-pin 150 comprises rod 152 and caudal fixation pins 154a and 154b. Rod 152 has embedded portion 152a and breakaway portion 152b, which are separated by breakaway notch 156. Fixation pins 154a and 154b have a depth $d_2$, which is preferably equal to 8 mm, and are preferably 1.5 mm in diameter at their base. Rod 152 preferably has a 2 mm×2 mm square cross section. Fixation pins 154a and 154b have tips or ends that are ogival as shown. Preferably, rod 152 and fixation pins 154a and 154b are fabricated from Tivanium®, however other suitable materials may be used.

Figure 12:
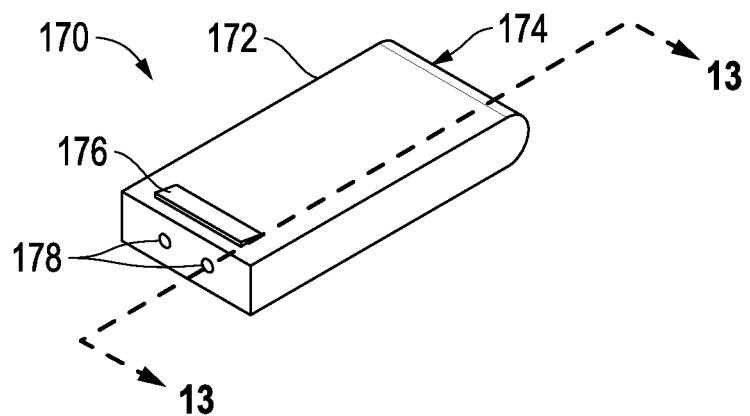
FIG. 12 depicts an isometric view of a first embodiment of a locking plug of the ILFD of FIG. 2.
Figure 13:
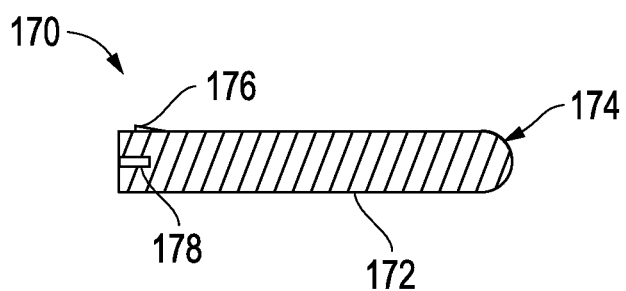
FIG. 13 depicts a cross-sectional view of the locking plug of FIG. 12.

Referring to FIGS. 12-13, a first embodiment 170 of a locking plug in accordance with the present invention is provided. Locking plug 170 comprises plug body 172 having rounded-insertion surface 174. Catch 176 is formed on one surface of plug body 172. Two grasper-pin openings 178 are provided in plug body 172 in the side opposite rounded-insertion surface 174. Preferably, locking plug 170 is 2 mm wide, 13 mm deep, and 6 mm high (for a 14 mm height implant body) or 8 mm high (for a 16 mm height implant body). Locking plug 170 is preferably fabricated from polyetheretherketone (PEEK).

Figure 14:
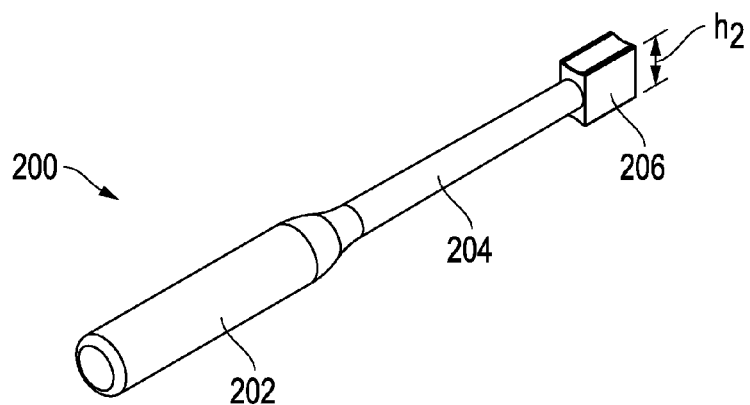
FIG. 14 depicts an isometric view of an implant-sizing tool.
Figure 15:
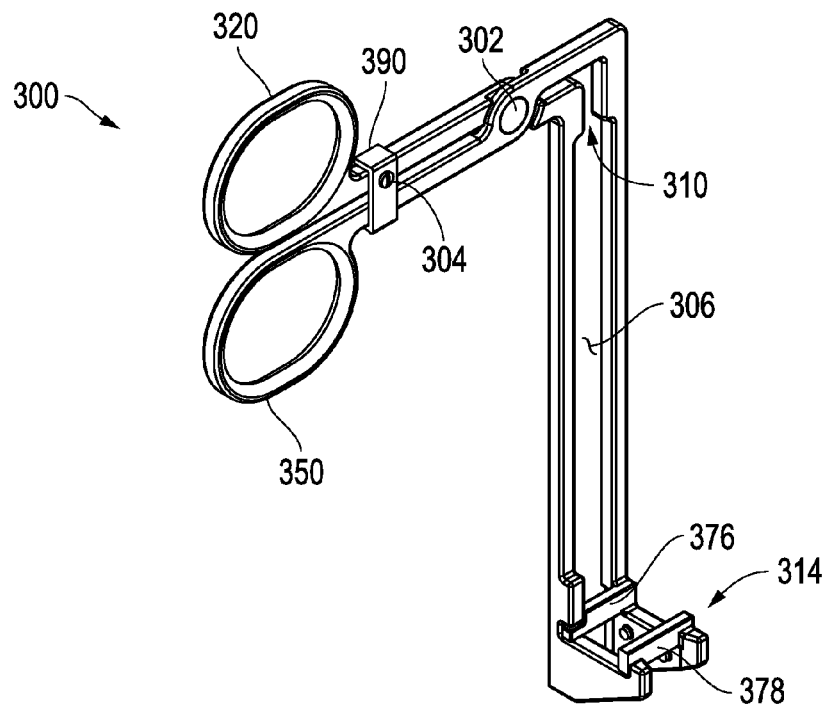
FIG. 15 depicts an isometric view of a first embodiment of an implant-grasper tool for use in combination with a first embodiment of a locking-plug inserter tool (see FIGS. 22-29) for implanting the ILFD illustrated in FIG. 2.
Figure 16:
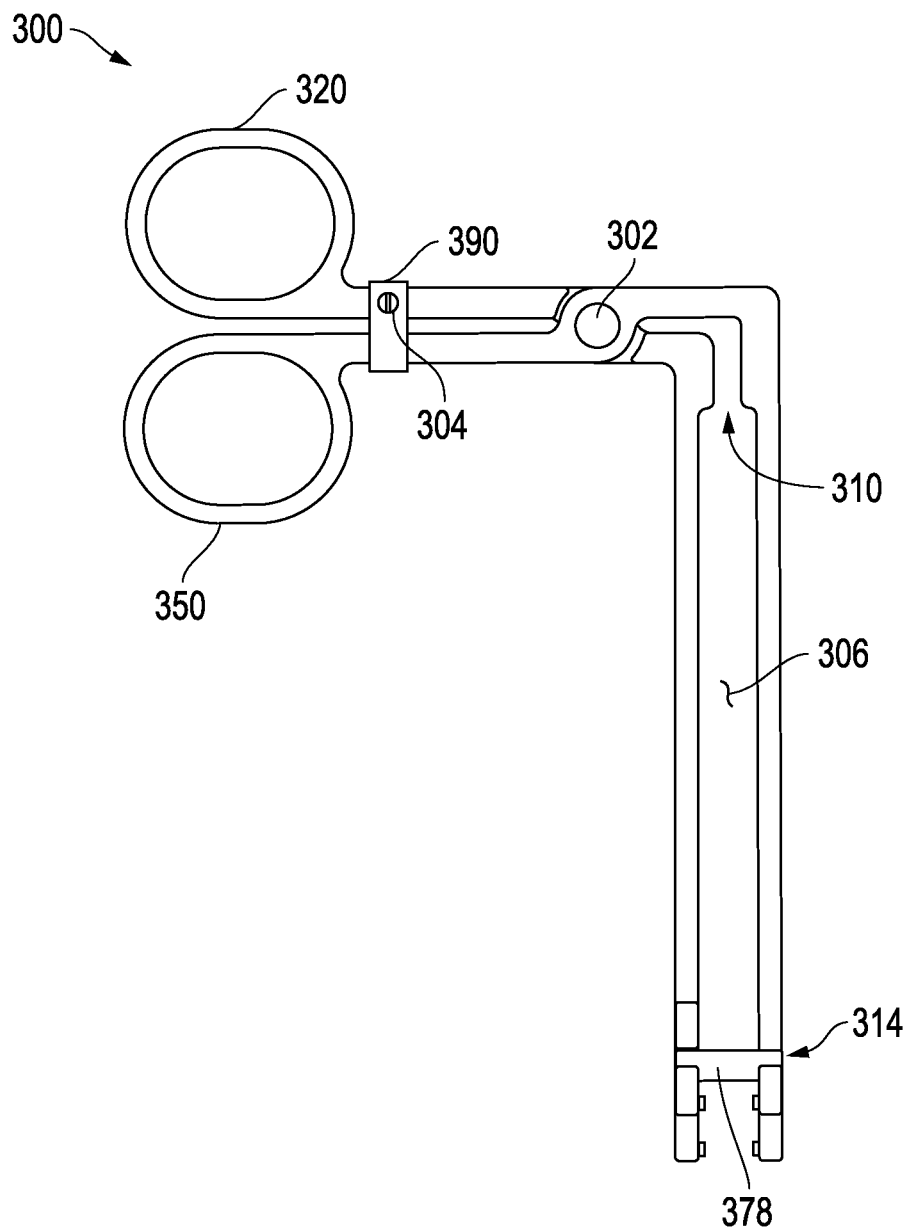
FIG. 16 depicts a side view of the implant-grasper tool of FIG. 15 in a closed position.
Figure 17:
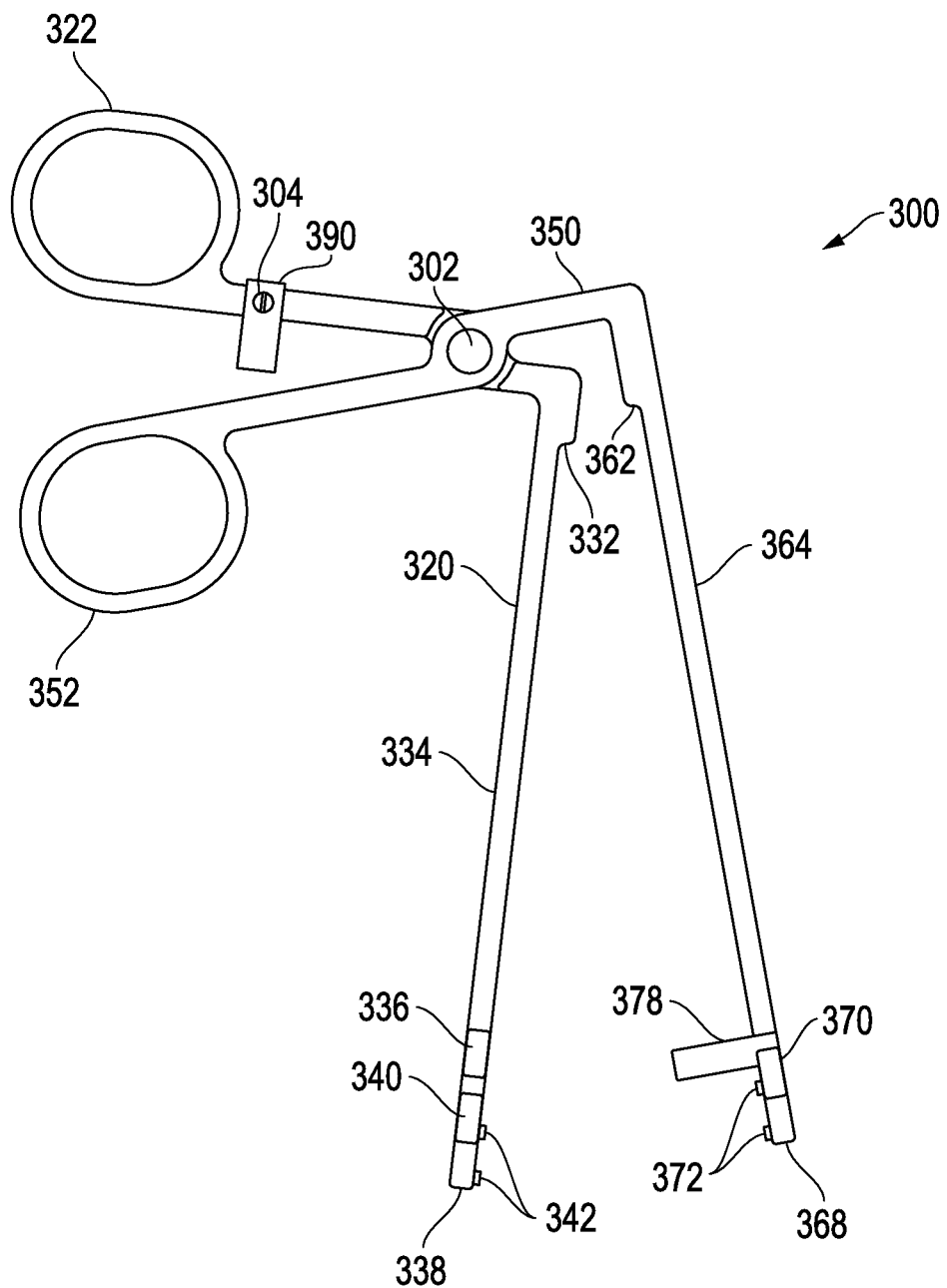
FIG. 17 depicts a side view of the implant-grasper tool of FIG. 15 in an open position.
Figure 18:
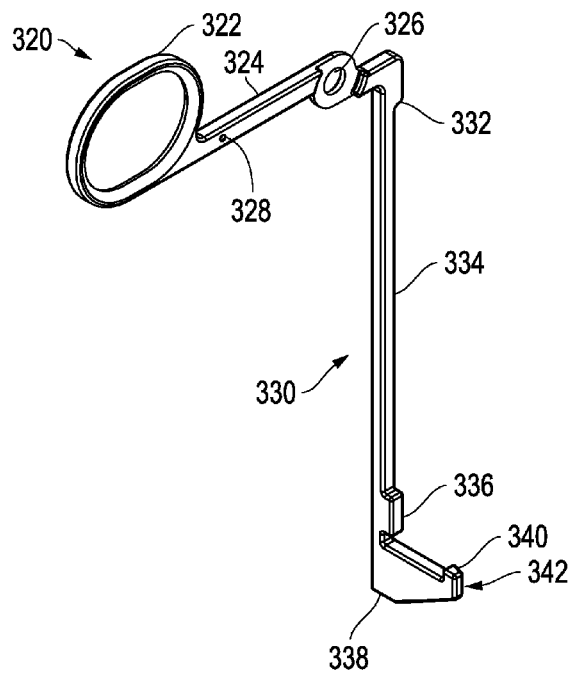
FIG. 18 depicts an isometric view of an upper element of the implant-grasper tool of FIG. 15.
Figure 19:
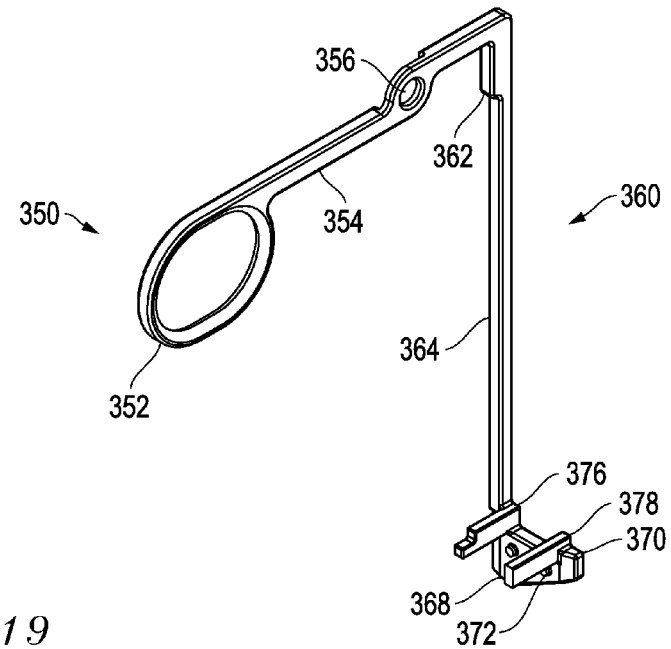
FIG. 19 depicts an isometric view of a lower element of the implant-grasper tool of FIG. 15.
Figure 20:
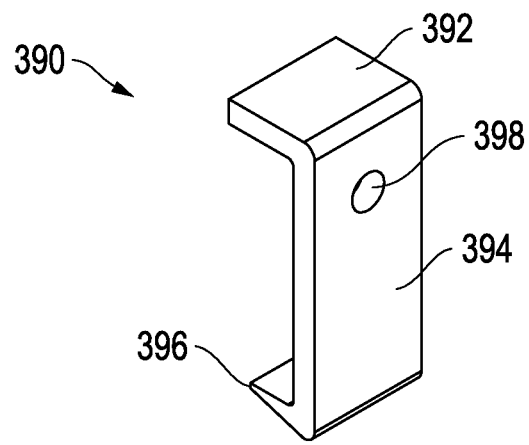
FIG. 20 depicts an isometric view of a grasper-lock mechanism of the implant-grasper tool of FIG. 15.
Figure 21:
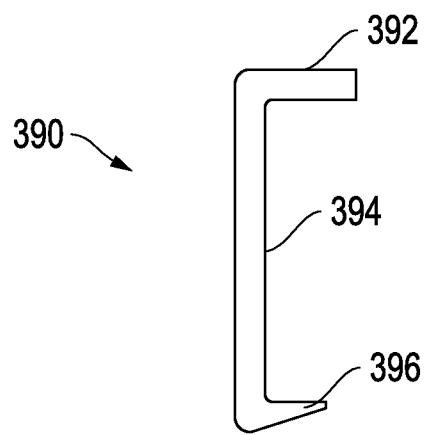
FIG. 21 depicts a side view of the grasper-lock mechanism of FIG. 20.
Figure 22:
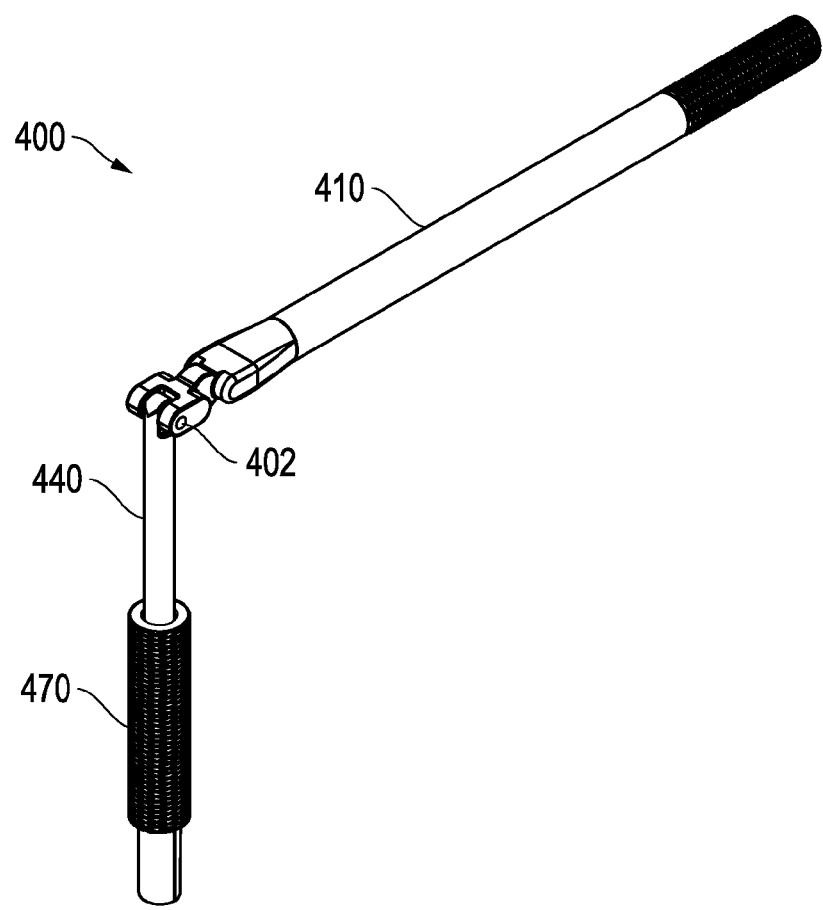
FIG. 22 depicts an isometric view of a first embodiment of a locking-plug inserter tool for use in combination with the implant-grasper tool of FIG. 15 for implanting the ILFD of FIG. 2.

Referring to FIG. 14, implant-sizing tool 200 is provided. Implant-sizing tool 200 comprises handle 202, handle linkage 204, and trial implant 206. Trial implant 206 has a threaded opening for connection with handle linkage 204 (not shown). Trial implant 206 is substantially similar to implant body 110. Trial implant 206 has height $h_2$. Preferably in practice, two trial implants are provided, one having height $h_2$ equal to 14 mm and another equal to 16 mm. Handle 202, handle linkage 204, and trial implant 206 are fabricated preferably from AISI 314L stainless steel.

Referring to FIGS. 15-21, a first embodiment 300 of an implant-grasper tool is provided in accordance with the present invention. Implant-grasper tool 300 comprises: upper element 320 pivotally connected to lower element 350 by fastener 302; slot 306 when implant-grasper tool 300 is in the closed position (see FIG. 16); fulcrum 310; and grasper portion 314. Components of implant-grasper tool 300 are preferably fabricated from AISI 314L stainless steel.

Upper element 320 comprises handle 322, handle linkage 324, fastener opening 326, lock-mechanism opening 328 (optional), and lower portion 330. Fulcrum protrusion 332 is formed at the medial end of lower portion 330 and is connected to grasper linkage 334. Grasper detent 336 is formed at the distal end of grasper linkage 334. Grasper plate 338 is connected to the distal end of grasper linkage 334 as shown and has grasper flange 340. Grasper pins 342 are formed on one side of grasper plate 338 and are configured to mate with grasper-pin openings 178 on implant body 110 (see FIG. 4).

Lower element 350 comprises handle 352, handle linkage 354, fastener opening 356, and lower portion 360. Fulcrum protrusion 362 is formed at the medial end of lower portion 360 and is connected to grasper linkage 364. Grasper plate 368 is connected to the distal end of grasper linkage 364 as shown and has grasper flange 370. Grasper pins 372 are formed on one side of grasper plate 368 and are configured to mate with grasper-pin openings 178 on implant body 110 (see FIG. 4). First grasper bar 376 is connected to the lower portion of grasper linkage 364 and grasper plate 368 as shown. Second grasper bar 378 is connected to grasper plate 368 and grasper flange 370 as shown. Grasper bars 376 and 378 protrude in parallel towards grasper plate 338 when implant-grasper tool 300 is in the closed position (see FIG. 15).

Optional, locking mechanism 390 is connected to upper element 320 at opening 328 by fastener 304 and is used to secure implant-grasper tool 300 in the closed position. Locking mechanism 390 comprises upper portion 392, lateral portion 394, and locking portion 396. Fastener opening 398 is formed in lateral portion 394. In yet other embodiments, locking mechanism may be connected to lower element 350 instead of upper element 320. Alternatively, other means for locking implant-grasper tool 300 in the closed position may be used.

Referring to FIGS. 22-29, a first embodiment 400 of a locking-plug inserter tool is provided. Locking-plug inserter tool 400 comprises handle element 410 pivotally connected to plunger element 440 by fastener 402. Components of locking-plug inserter 400 are preferably fabricated from AISI 314L stainless steel.

Figure 23:
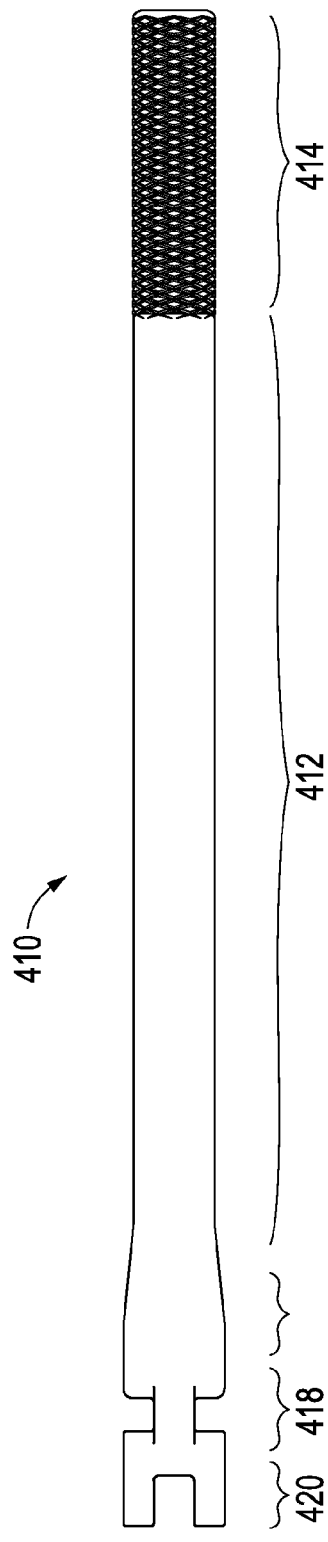
FIGS. 23-24 depict side views of a handle element of the locking-plug inserter tool of FIG. 22.
Figure 24:
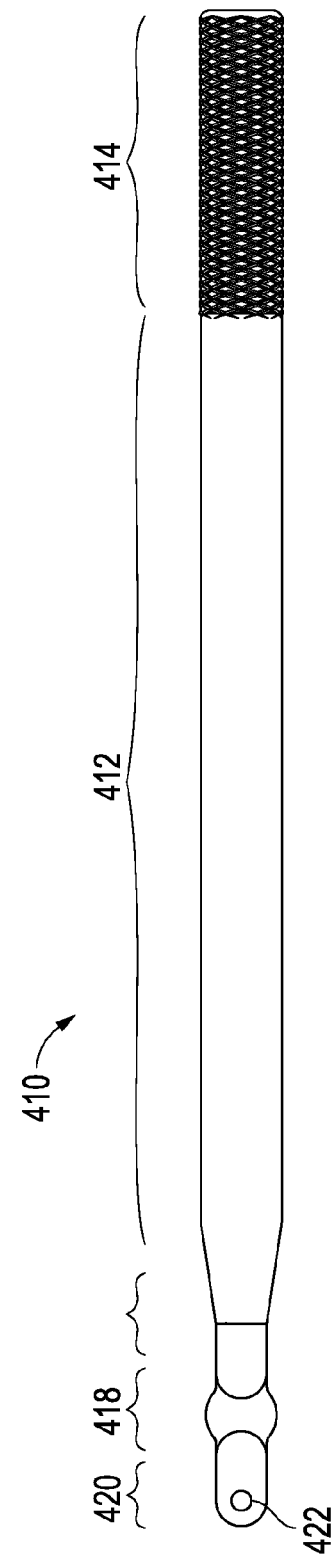

Handle element 410 comprises linkage portion 412, grip portion 414, pivot-point-engagement portion 418, and fastener portion 420 as shown (see FIGS. 23-24). Grip portion 414 is preferably knurled for enhanced gripping. Pivot-point-engagement portion 418 is configured to pivotally engage fulcrum 310 of implant-grasper tool 300.

Figure 25:
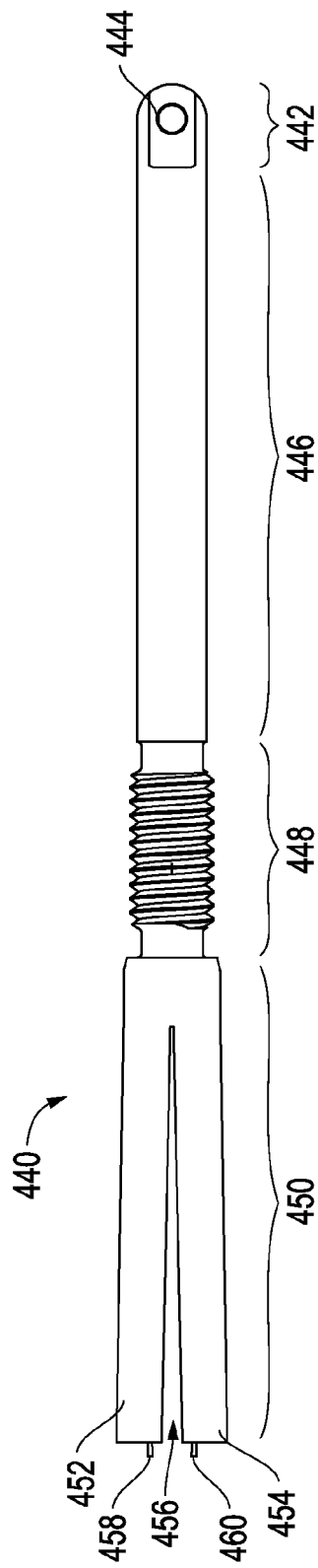
FIGS. 25-26 depict side views of a plunger element of the locking-plug inserter tool of FIG. 22.
Figure 26:
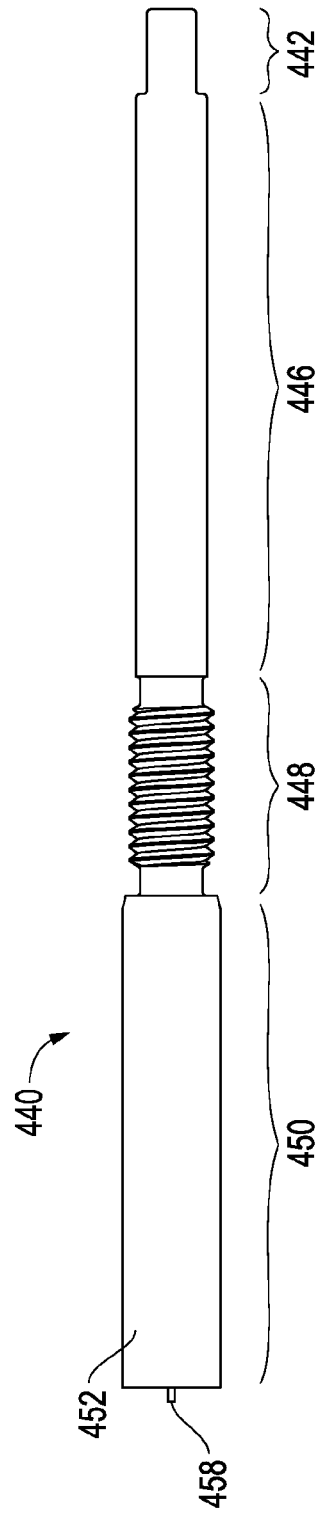

Plunger element 440 comprises fastener portion 442 having fastener opening 444, linkage portion 446, threaded portion 448, and deflectable-grasper portion 450 (see FIGS. 25-26). Deflectable-grasper portion 450 has first deflectable member 452 and second deflectable member 454 defining closable gap 456 as shown (see FIG. 25). Grasper pins 458 and 460 are formed on the ends of deflectable members 452 and 454, respectively, and are configured for engaging grasper-pin openings 178 of locking plug 170.

Figure 27:
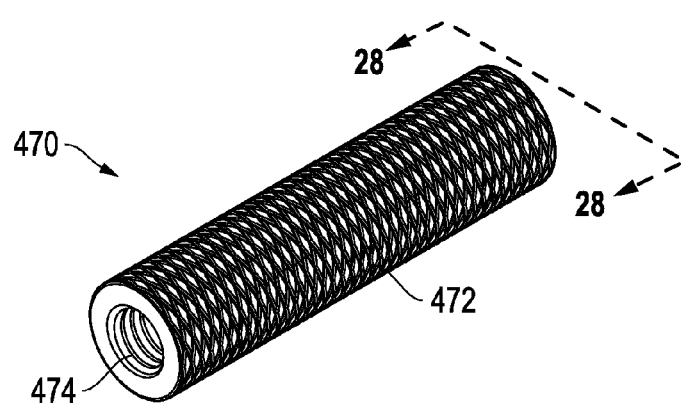
FIG. 27 depicts an isometric view of a collet element of the locking-plug inserter tool of FIG. 22.
Figure 28:
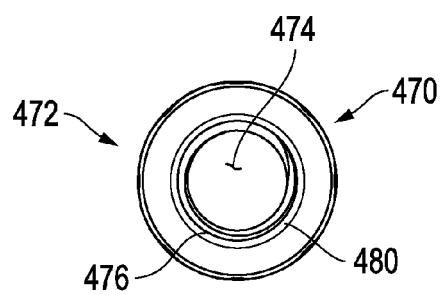
FIG. 28 depicts a side view of the collet element of FIG. 27.
Figure 29:
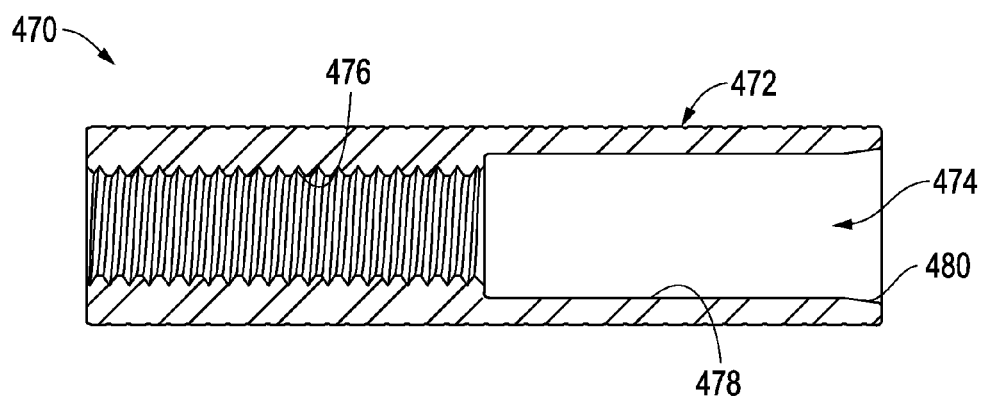
FIG. 29 depicts a cross-sectional view of the collet element of FIG. 27 taken along section line 28-28.
Figure 48:
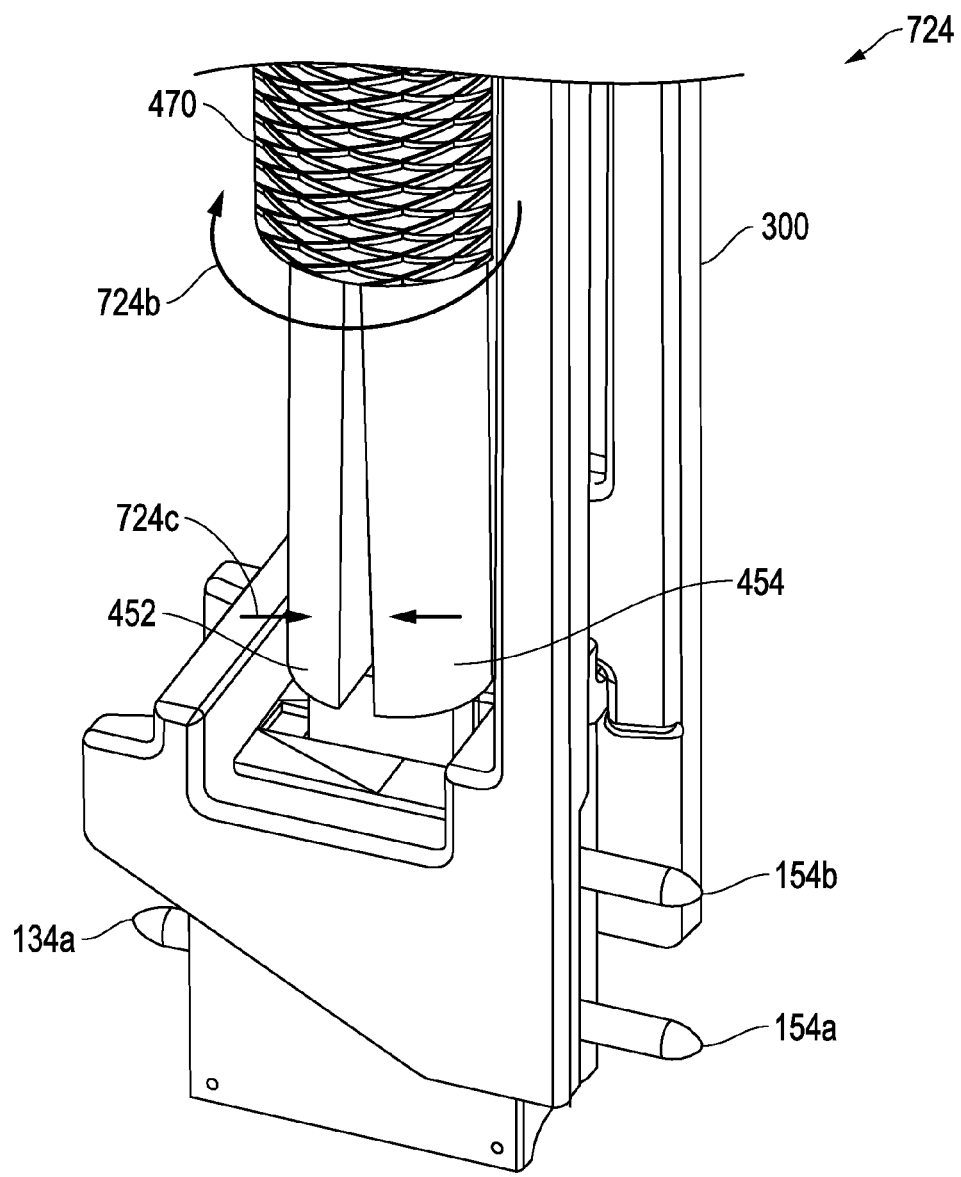
Figure 49:
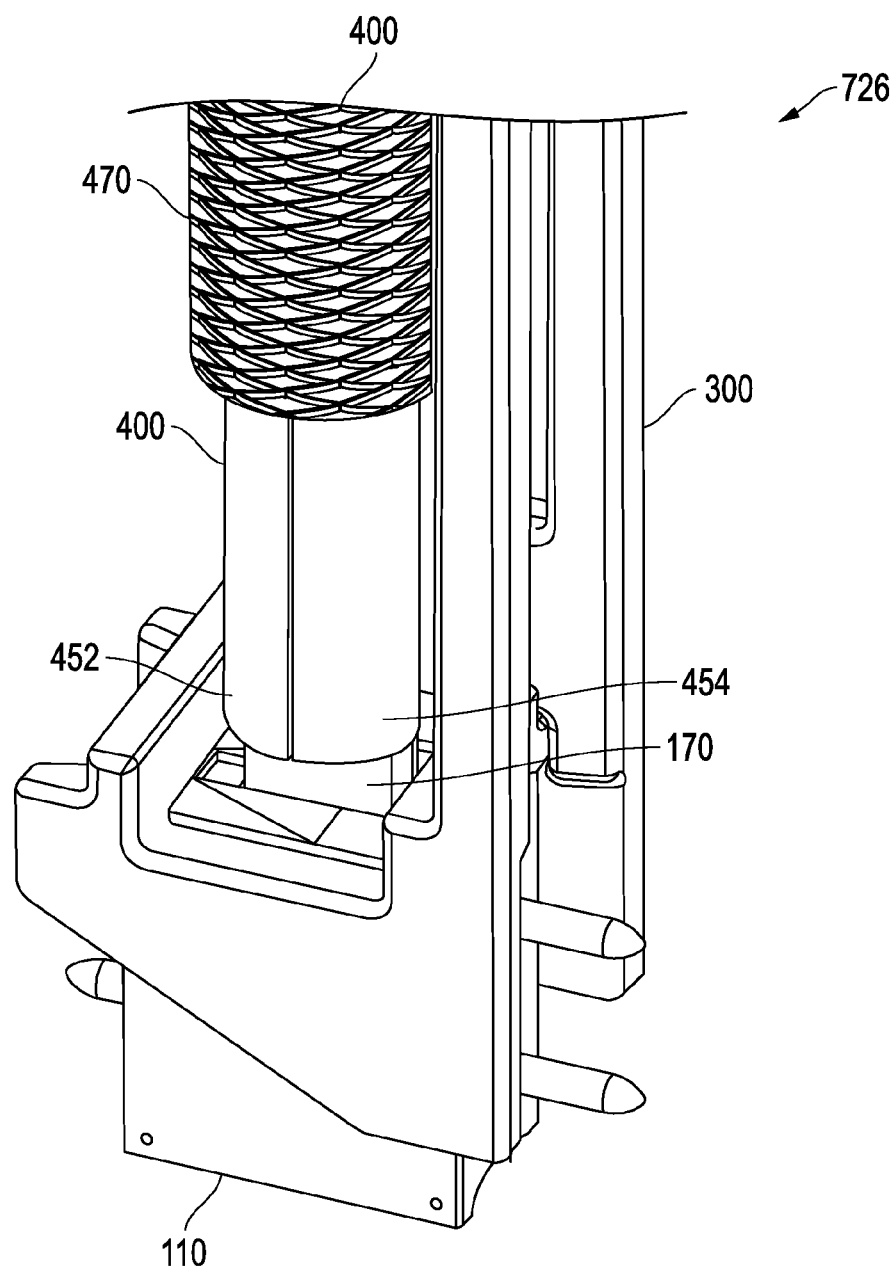
Figure 50:
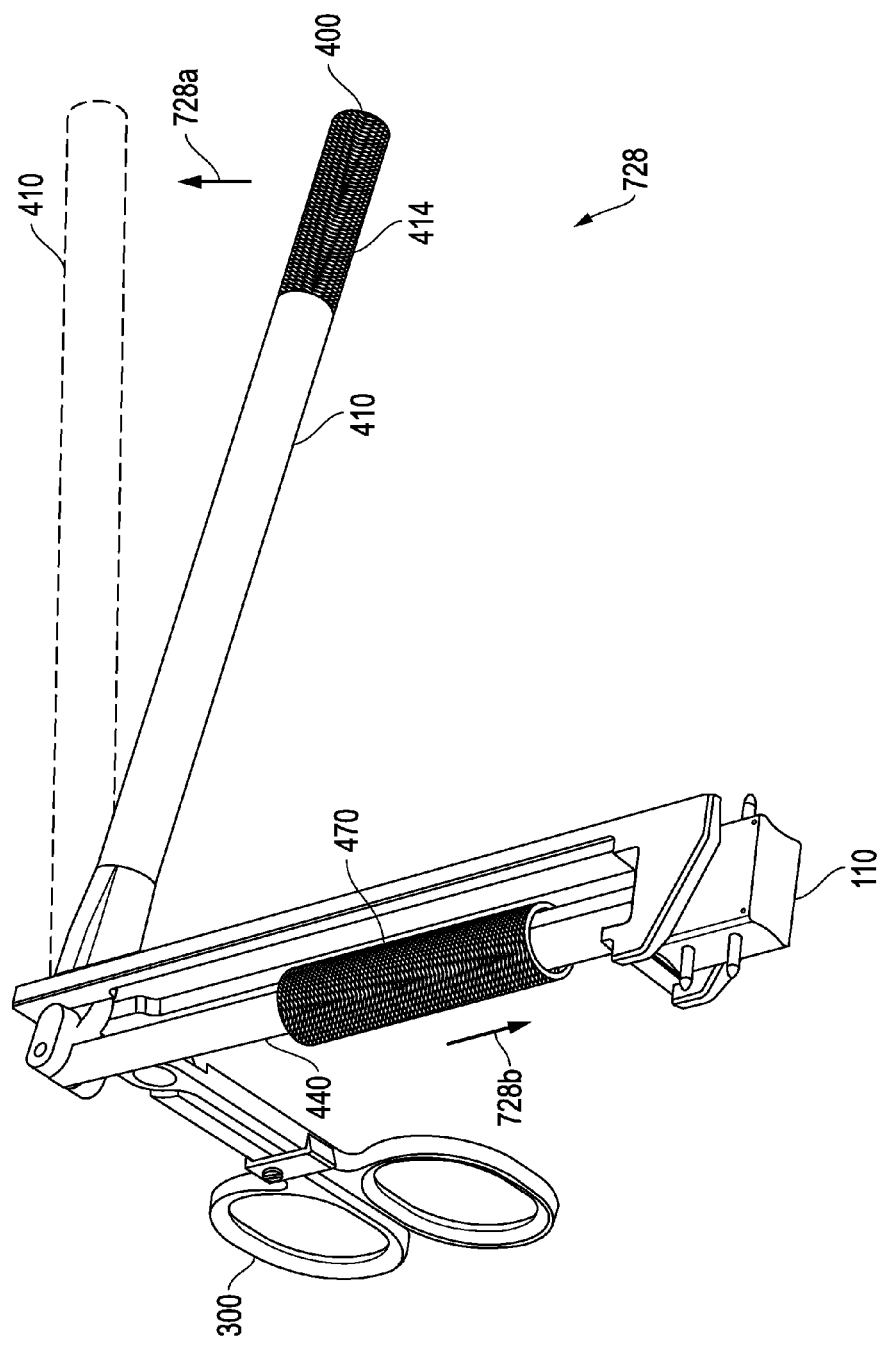
Figure 51:
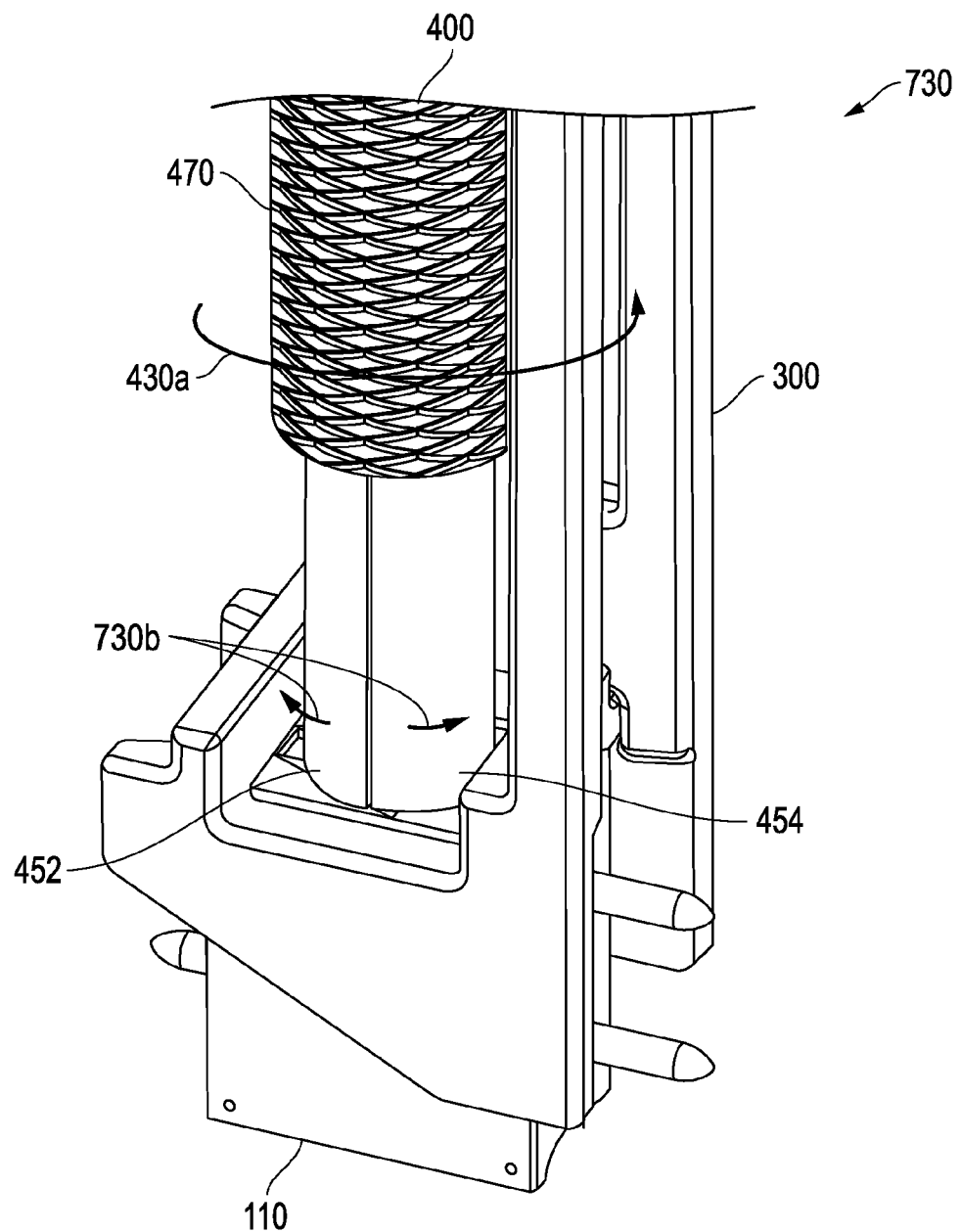

Collet 470 is provided and is generally cylindrical (see FIGS. 27-29). Collet 470 has grip surface 472 and hollow interior 474. Grip surface 472 is preferably knurled for enhanced gripping. Threaded portion 476 is provided and configured for threaded engagement with threaded portion 448 of plunger element 440. Clamping portion 478 having cambered portion 480 is also provided and is configured to urge deflectable members 452 and 454 together when collet 470 is rotated, thus resulting in a clamping force to secure locking-plug 170 to grasper portion 450 of plunger element 440 (see FIG. 48).

Figure 30:
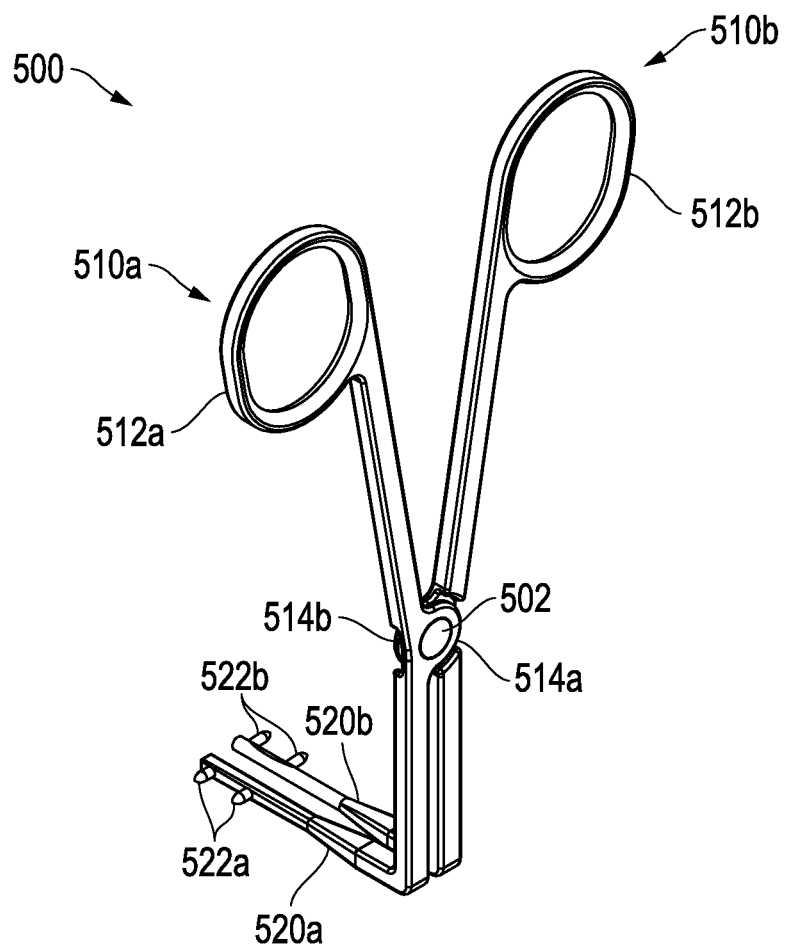
FIG. 30 depicts an isometric view of a bone-punch tool for use during implantation of the ILFD of FIG. 2.
Figures 31, 32:
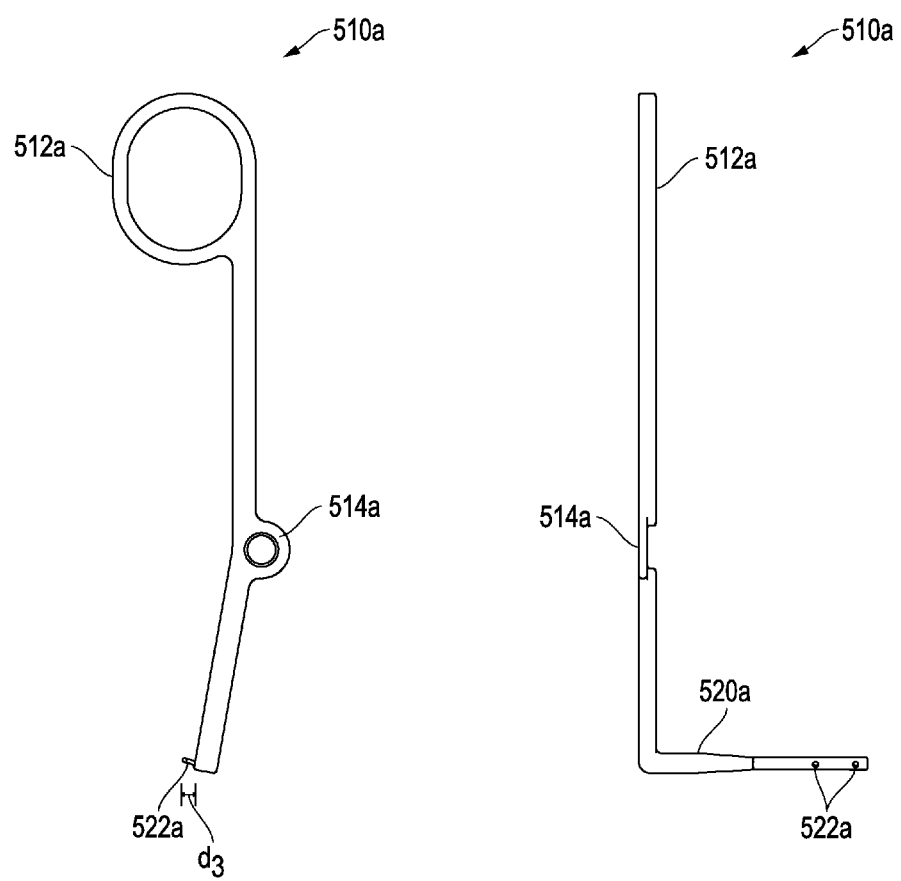
FIGS. 31-32 depict side views of an element of the bone-punch tool of FIG. 30.

Referring to FIGS. 30-32, bone-punch tool 500 is provided. Bone-punch tool 500 comprises first and second elements 510a and 510b pivotally connected by fastener 502. First element 510a comprises grip portion 512a, fastener-opening portion 514a, and punch-pin linkage portion 520a. Punch pins 522a are connected to punch-pin linkage portion 520a and protrude outward by depth $d_3$, which is preferably about 3 mm. Punch pins 522a have ends or tips that are ogival. Second element 510b is substantially identical to first element 510a. Components of bone-punch tool 500 are preferably fabricated from AISI 314L stainless steel.

Figure 33:
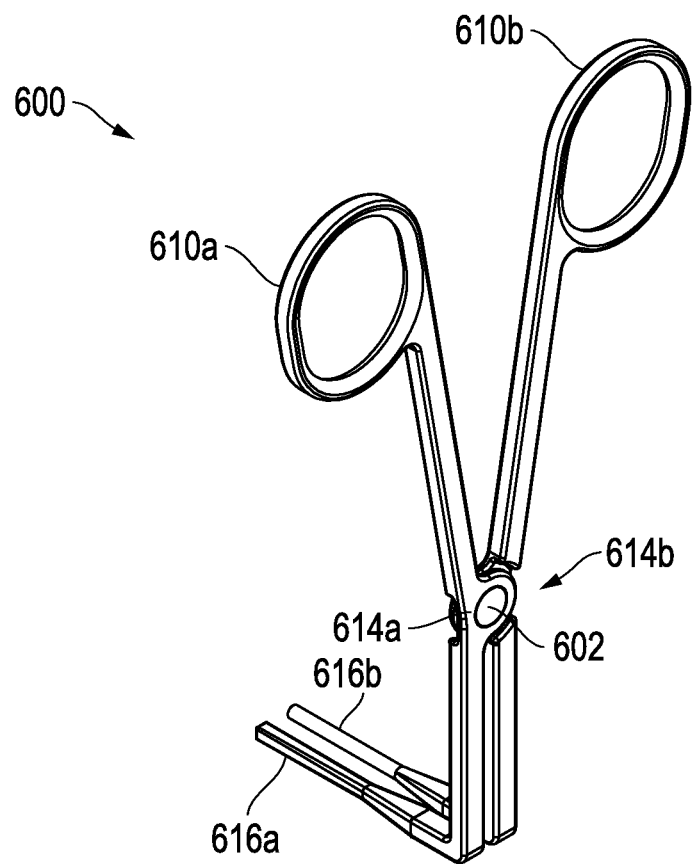
FIG. 33 depicts an isometric view of a pin-inserter tool for use during implantation of the ILFD of FIG. 2.
Figures 34, 35:
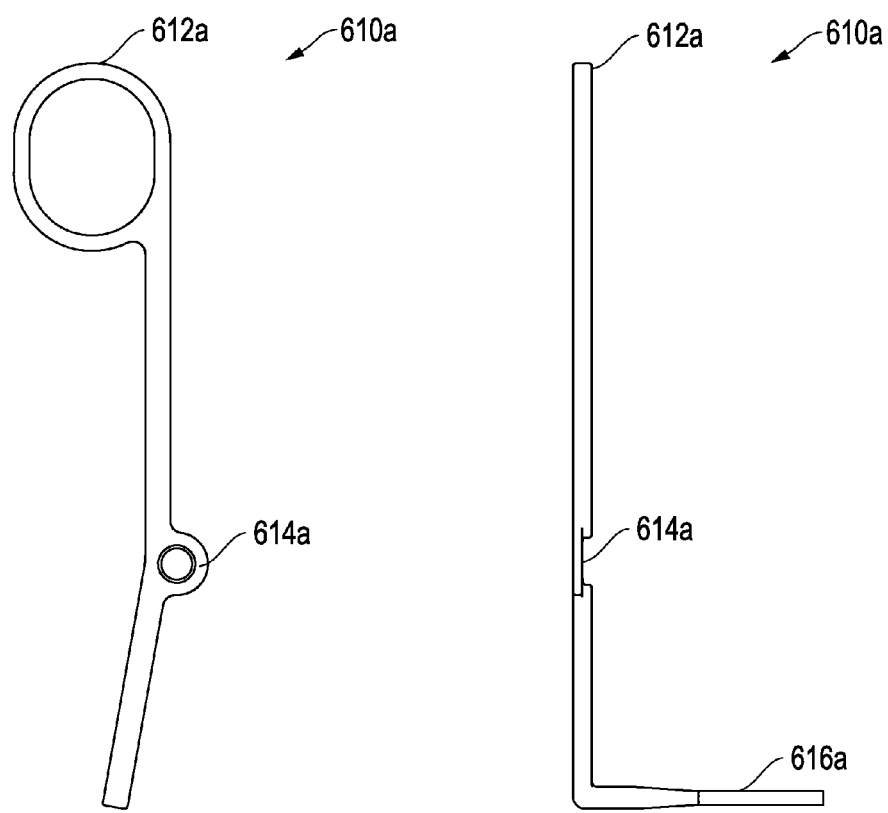
FIGS. 34-35 depict side views of an element of the pin-inserter tool of FIG. 33.
Figure 36:
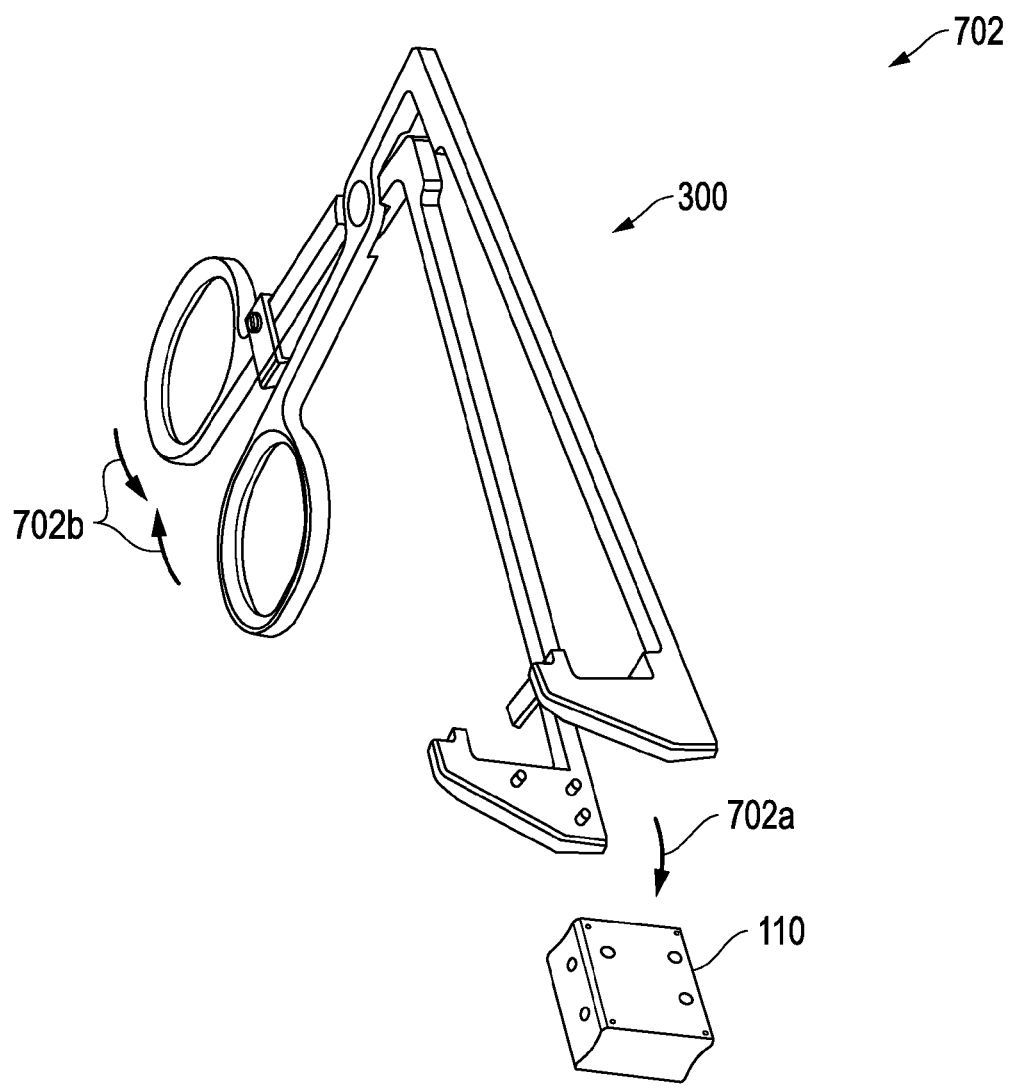
FIGS. 36-52 depict perspective views exemplifying the sequence of steps for implanting the ILFD of FIG. 2 using tooling shown in FIGS. 14-35.

Referring to FIGS. 33-35, pin-inserter tool 600 is provided. Pin-inserter tool 600 comprises first and second elements 610a and 610b pivotally connected by fastener 602. First element 610a comprises grip portion 612a, fastener-opening portion 614a, and camming portion 616a. Second element 610b is substantially identical to first element 610a. Components of pin-inserter tool 600 are preferably fabricated from AISI 314L stainless steel.

Method of Implantation

To begin, the patient is administered general anesthesia and intubated, then placed in the prone position preferably on either a Jackson table or a radiolucent Wilson frame. After appropriate positioning and padding of the patient's extremities, the patient's position may be adjusted to reduce the degree of lumbar lordosis. The patient's lumbar area to be treated is then given a sterile prep and draped.

Following appropriate pre-surgery protocol to confirm the patient's identification and the disc level for treatment, a sterile-draped C-arm is brought into the field and placed in a lateral position. An external marker is used and the surgical level identified. A mark is made on the patient's skin directly posterior to the appropriate disc level. An approximately 3 cm midline incision is then made with a scalpel centered over the mark. Electrocautery may be used to control bleeding and to dissect through the subcutaneous tissues down to the patient's lumbar fascia. The disc level is again confirmed preferably by lateral fluoroscopic image.

Next, the fascia is carefully dissected from each side of the spinous processes of the selected level and taken down to the laminae. The interspinous ligament is then resected and the inferior overhang of the proximal spinous process is trimmed with a rongeur such that it is parallel to the superior edge of the spinous process on the distal vertebra. Trimming is continued until either an appropriate sized ILFD 100 will fit snugly between the spinous processes with moderate force. The size required will depend upon the patient size and anatomy. Preferably, at least two sizes of ILFDs 100 are available, preferably one having heights $h_1$ equal to 14 mm and or 16 mm. Implant-sizing 200, with the appropriate sized trial implant 206, is inserted to test whether an appropriate fit has been achieved.

Next, decompression procedures are performed. The ligamentum flavum is dissected from the underside of the rostral vertebra. Then, preferably using a Woodson elevator, the median raphe is carefully explored with care not to enter the dural sac. The central portions of the ligamentum flavum are then pulled distally, morselized, and removed with Kerrison rongeurs. If necessary, a laminotomy may be performed in order to complete the decompression of the central spinal canal and to provide appropriate bearing surfaces for the implant. It is preferable that the laminotomy not exceed the extent of the trimming of the spinous processes as it is advantageous that the device be in contact with the laminae due to their superior strength relative to the spinous process.

While carefully protecting the dural sac, the lateral slip of the ligamentum flavum may be removed. This will allow visualization of the ventral portion of the spondyloapophyseal joint and appropriate bony resection may be performed until the lateral recess is decompressed and the nerve root can be followed out into the neural foramen using preferably a ball tipped Murphy probe. The surgeon then may switch sides and repeat the process on the contralateral side. Following confirmation of decompression using Murphy probes, hemostasis may be achieved.

Referring to FIGS. 36-52, a preferred method 700 of implanting ILFD 100 in a spine 10 (see FIG. 1) of a patient using implant-sizing tool 200 (discussed above), implant-grasper tool 300, locking-plug inserter tool 400, bone-punch tool 500, and pin-inserter tool 600 is described. For clarity, spine 10 is shown only in FIG. 37 and omitted from FIGS. 38-52.

Figure 37:
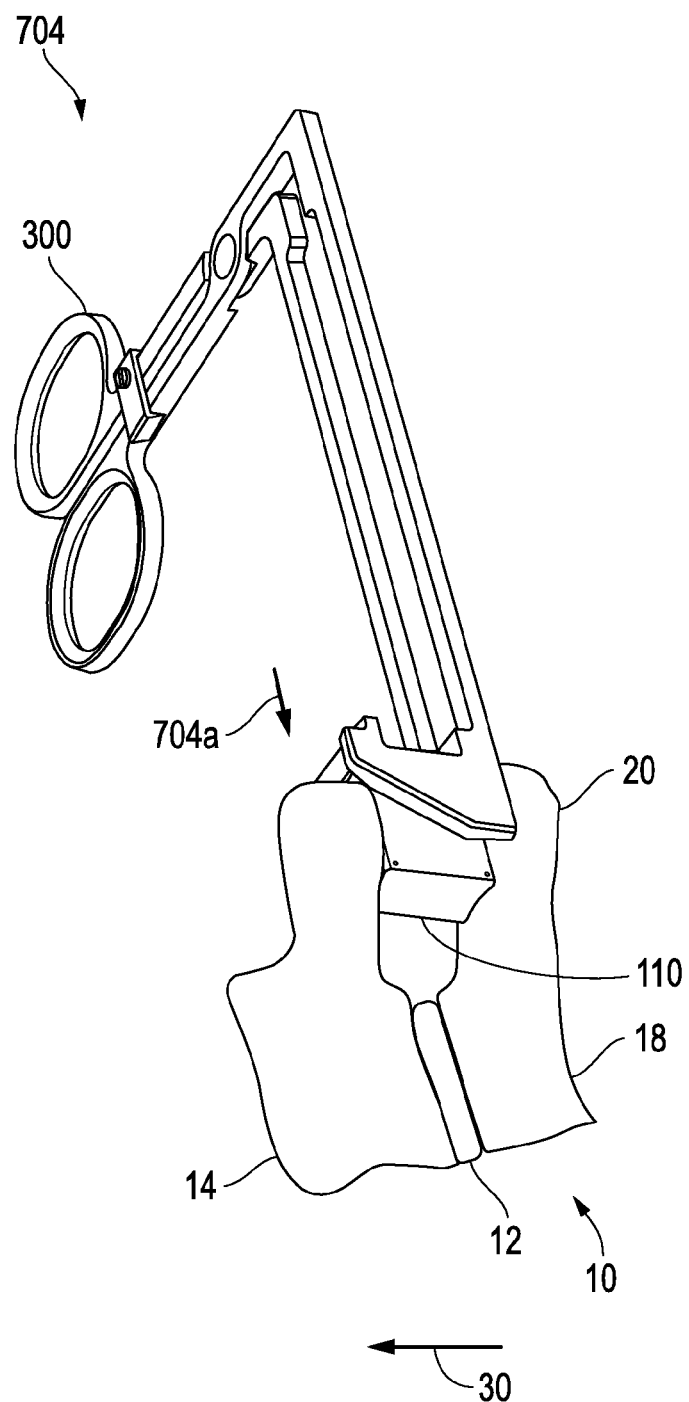
Figure 38:
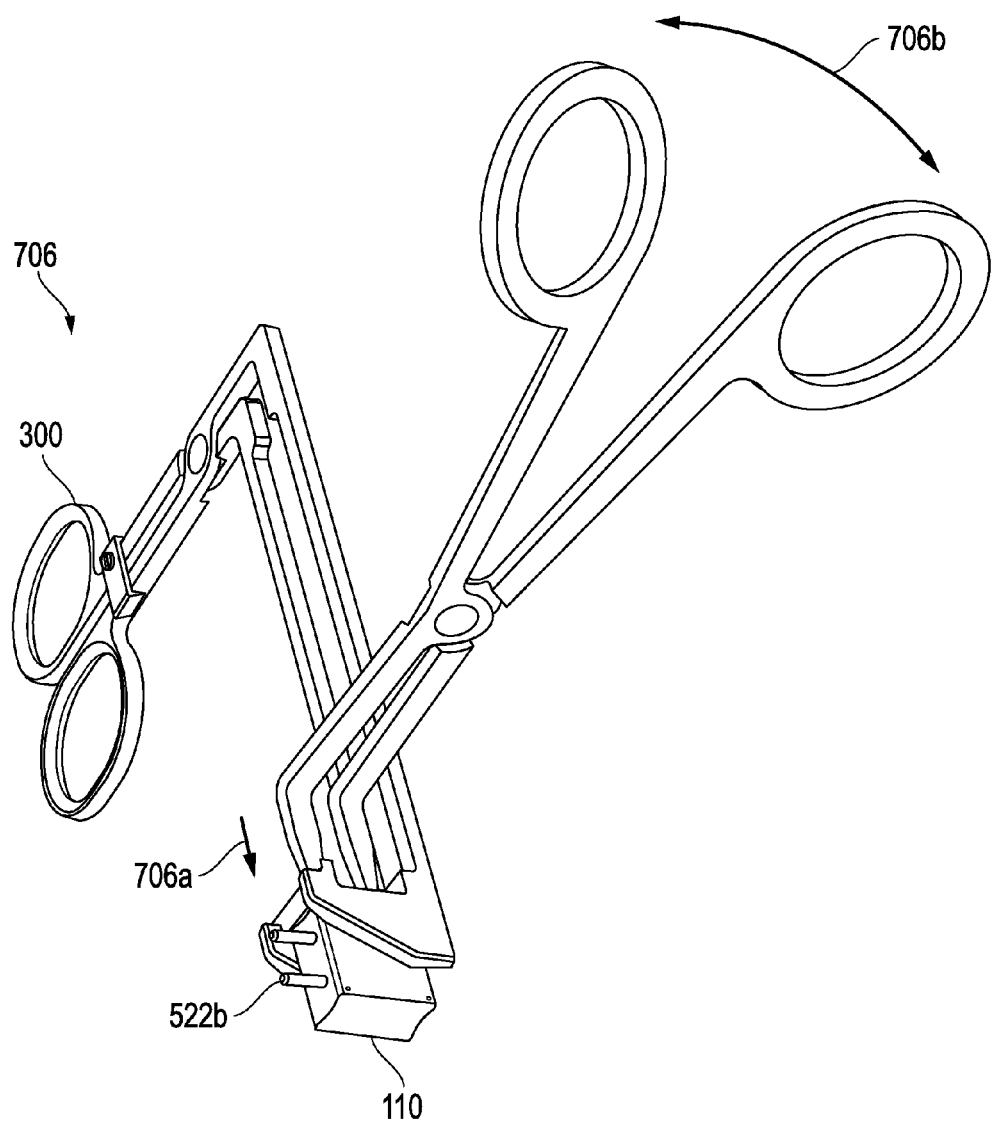
Figure 39:
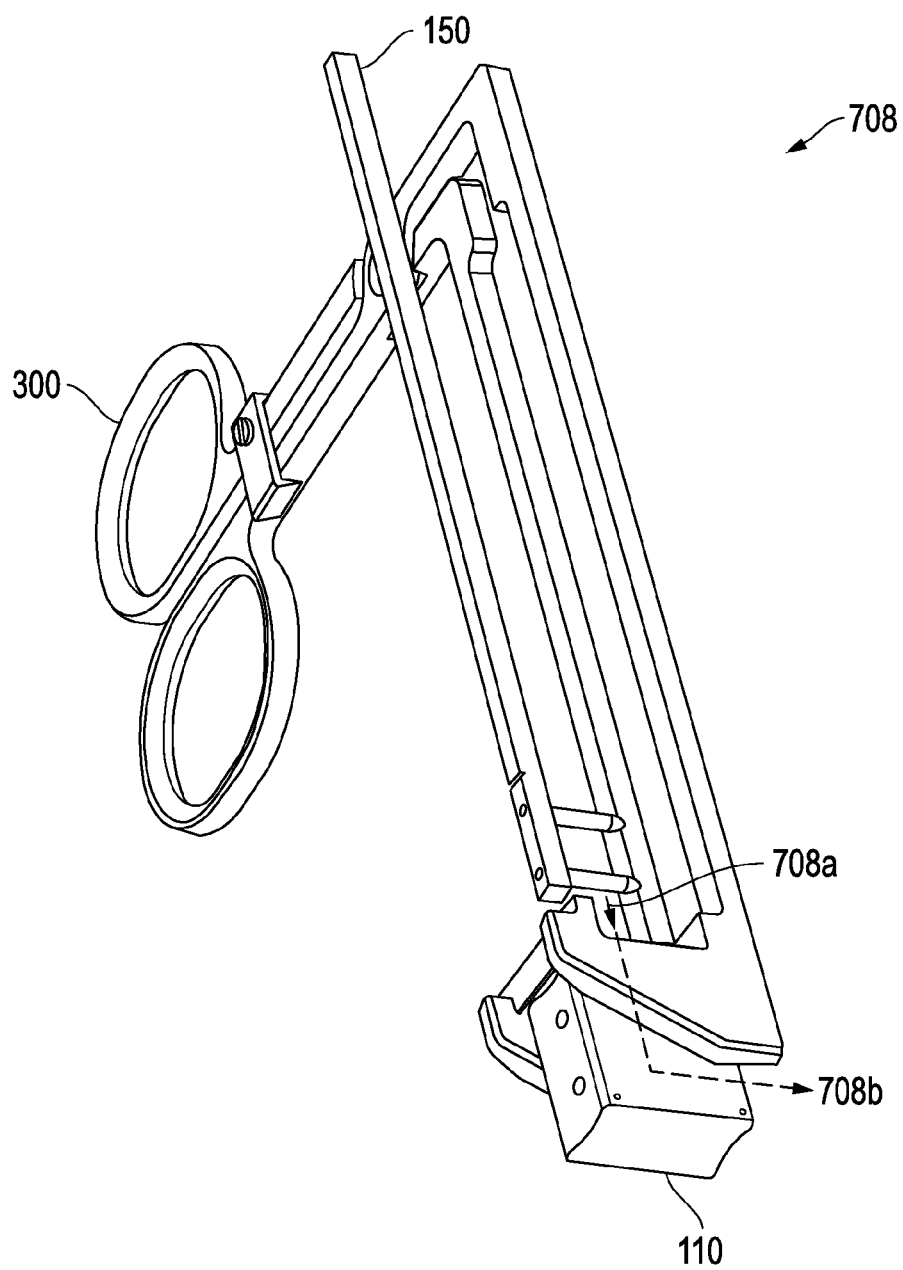
Figure 40:
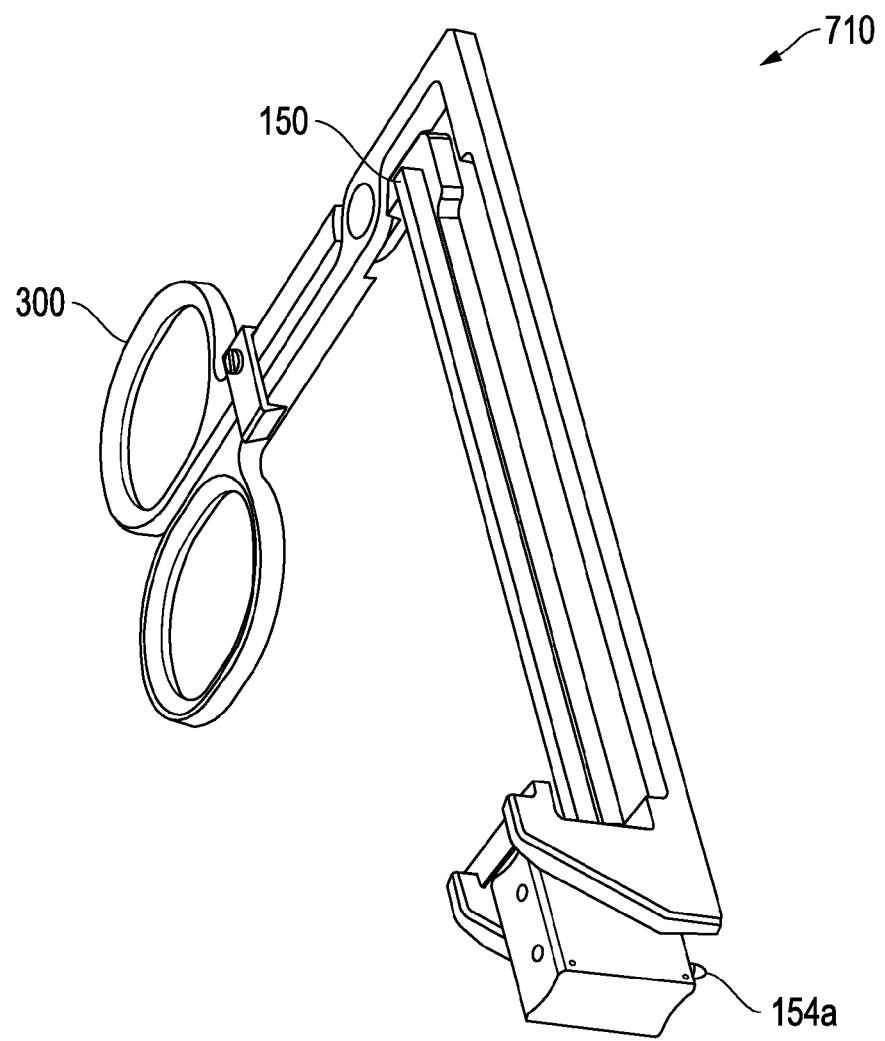
Figure 41:
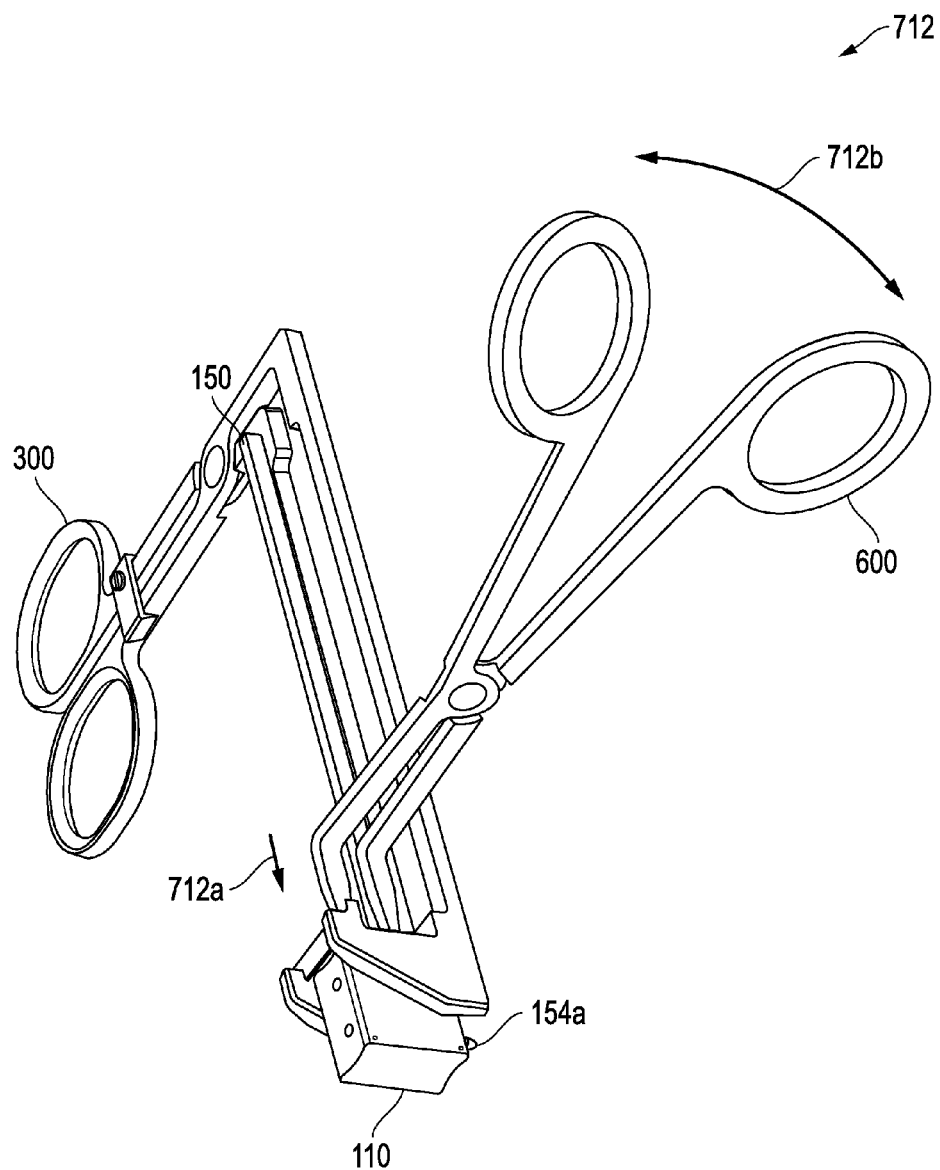
Figure 42:
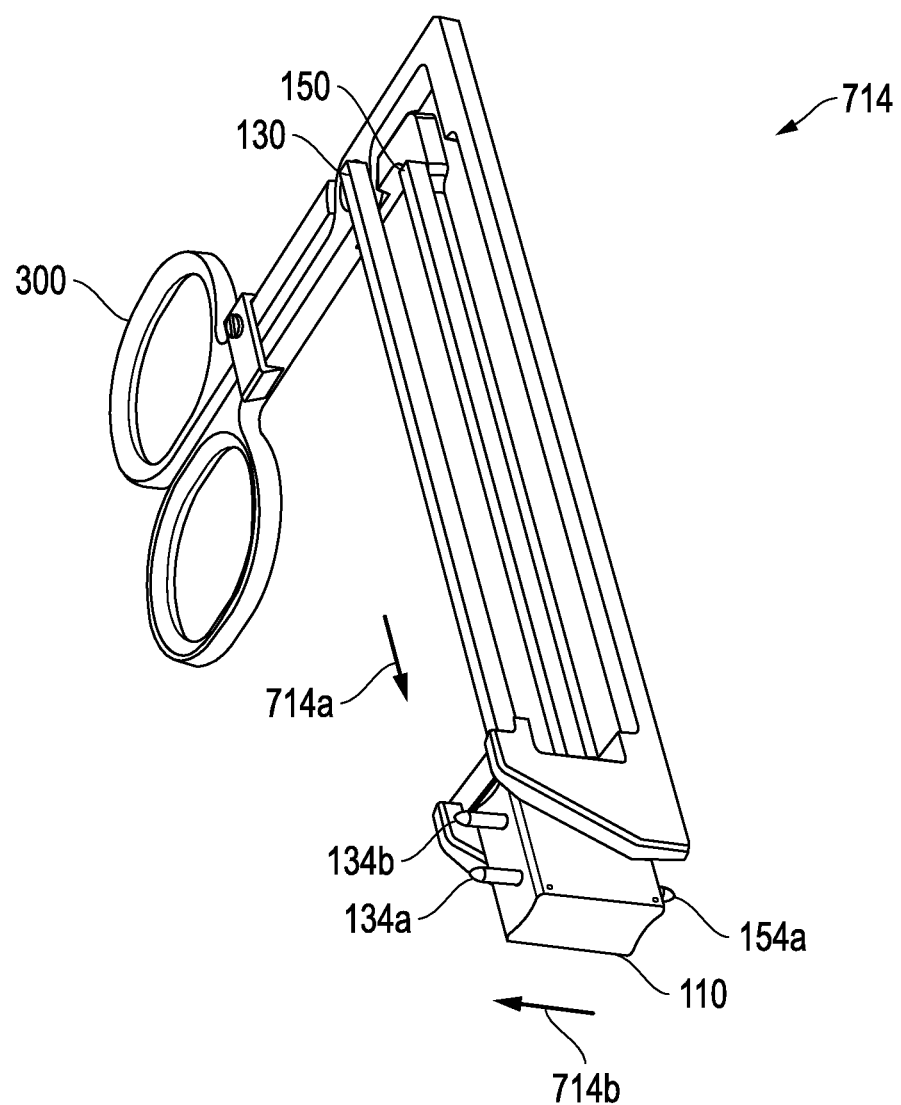
Figure 43:
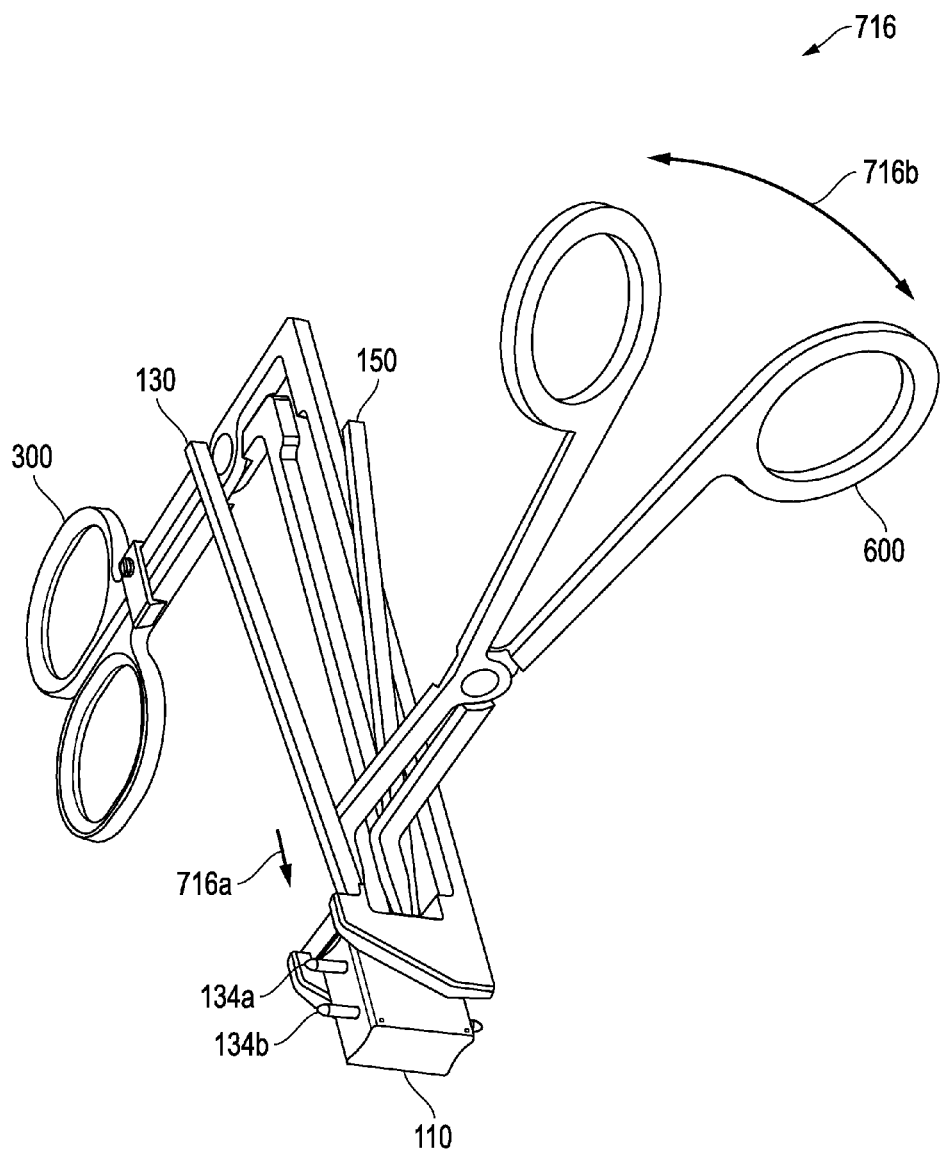
Figure 44:
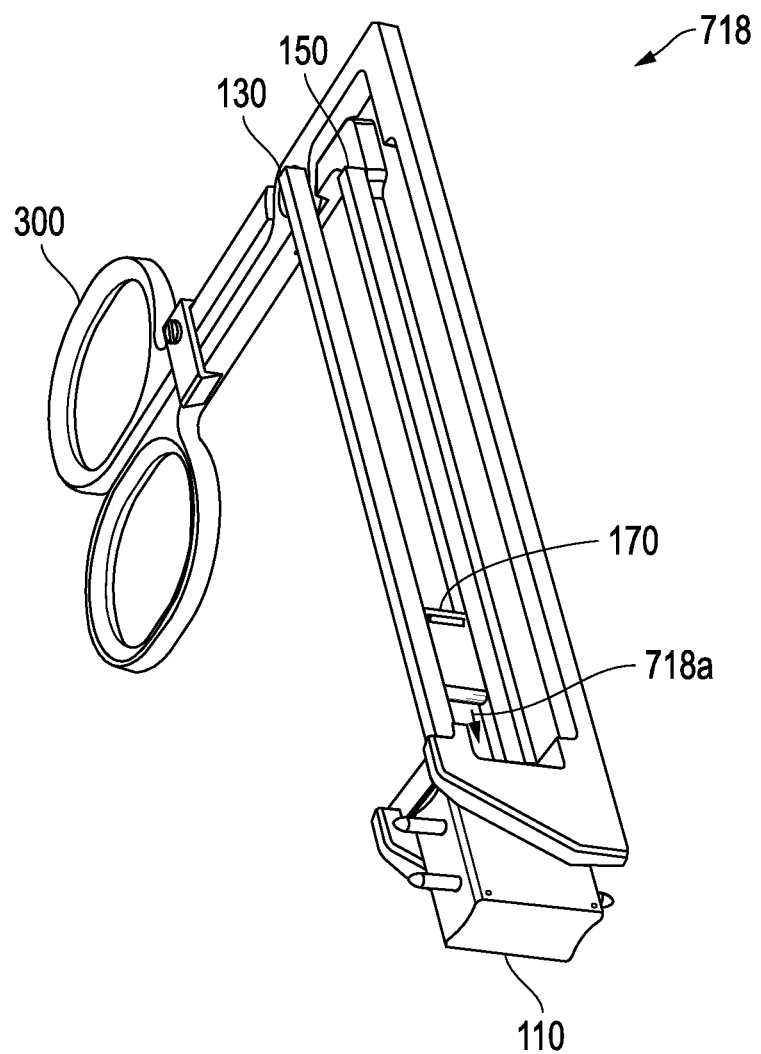
Figure 45:
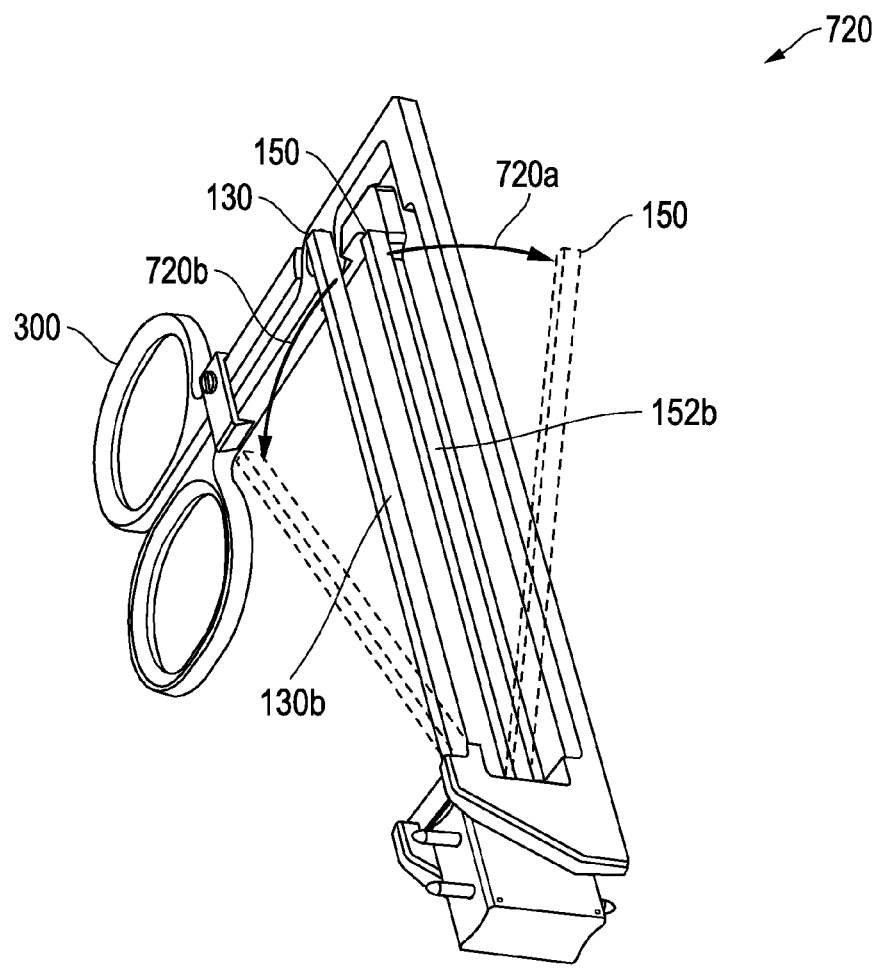
Figure 46:
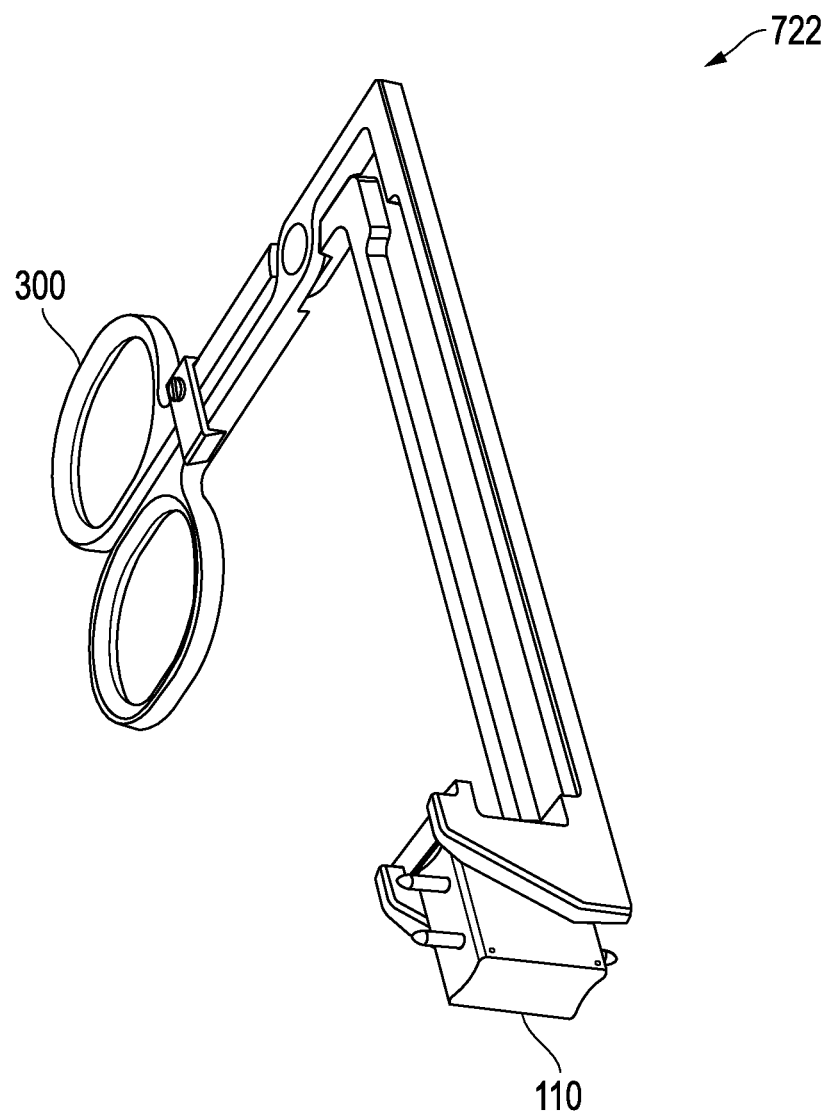
Figure 47:
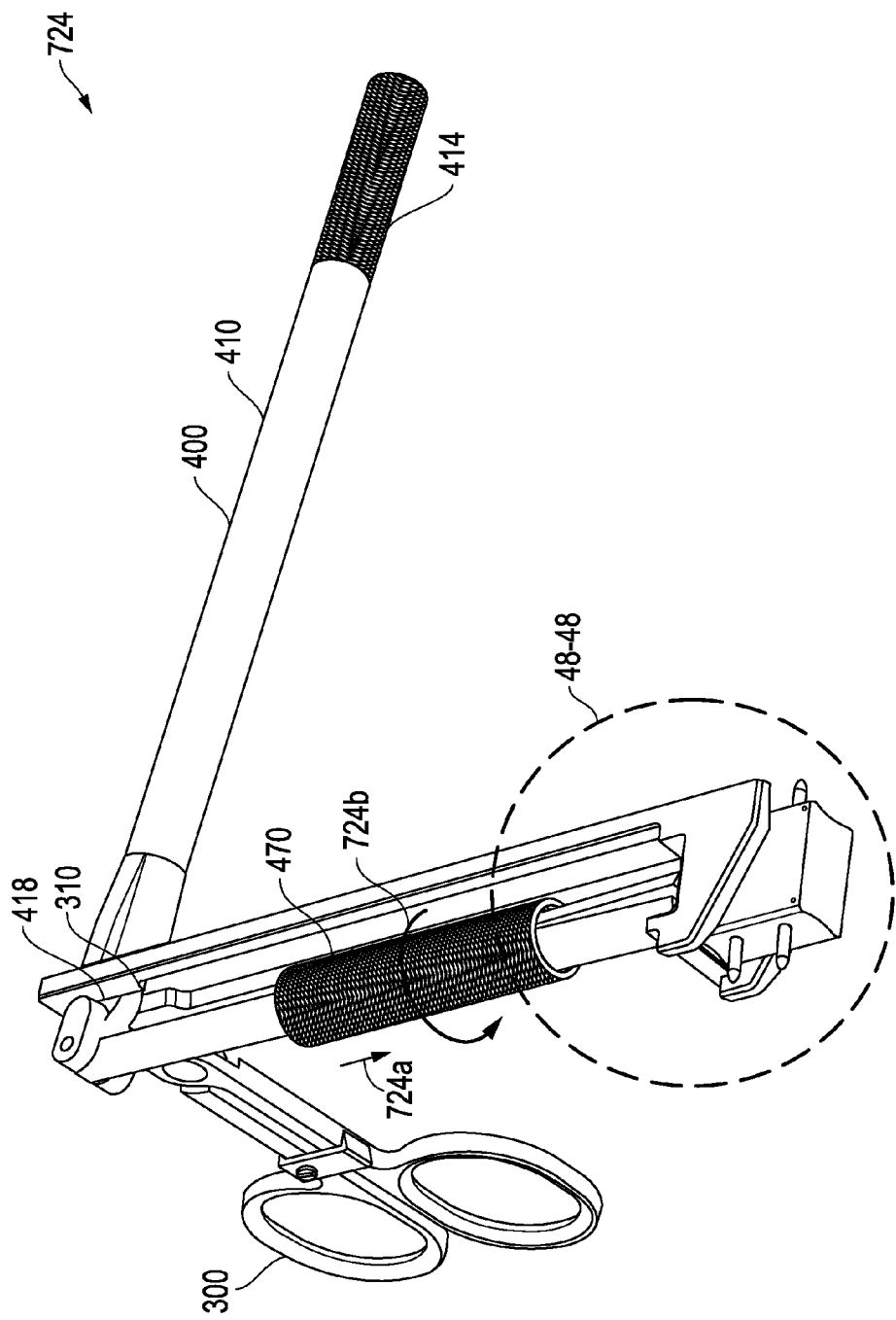

The appropriately sized implant body 110 is selected. Then, it is grasped using implant-grasper tool 300 and locking mechanism 390 is engaged (step 702). Using implant-grasper tool 300 having grasped implant-body 110, implant body 110 is positioned between the patient's spinous processes 16 and 20 and at the appropriate depth so that ventral surface 112f of implant body 110 is between the patient's laminae (step 704). When implant body 110 is oriented correctly, orientation indicator 120 on implant body 110 indicates the direction of the patient's head as shown by arrow 30 (FIG. 37). Preferably, direct vision and lateral fluoroscopy are used to ensure that implant body 110 is at the appropriate depth, with ventral surface 112f firmly between the laminae but without any contact with, or compression of, the dural sac.

Preferably, the surgeon positions himself on the side of the patient so that his dominant hand is caudal to the operative site. He then stabilizes implant-grasper tool 300 with his non-dominant hand and uses his dominant hand to insert bone-punch tool 500 (step 706a) and makes starter holes in the spinous process (step 706b). Fixation-pin assemblies 130 and 150 are then inserted one at a time (steps 708a, 708b, 714a, and 714b) and pressed into place using pin-inserter tool 600 (steps 712a, 712b, 716a, and 716b). Fixation-pin assemblies 130 and 150 may be inserted in either order.

Next, locking plug 170 is inserted partially into implant body 110 (step 718). Then, preferably, breakaway portions 132b and 152b of fixation-pin assemblies 130 and 150, respectively, are bent until failure at breakoff notches 136 and 156 (step 720). Alternatively, breakaway portions 132b and 152b may be cut off. Breakoff notches 136 and 156 may be discarded (step 722).

Locking-plug inserter tool 400 is inserted into implant-grasper tool 300. This is done by first inserting handle element 410 of locking-plug inserter tool 400 through slot 306 of implant-grasper tool 300, then rotating locking-plug inserter tool 400 such that pivot-point engagement portion 418 engages fulcrum 310 (see FIG. 47). Alternatively, plunger element 440 may be initially disassembled from handle element 410 and fastened to handle element 410 once properly inserted into implant-grasper tool 300. Once grasper pins 458 and 460 of locking-plug inserter tool 400 engage grasper-pin openings 178 of locking plug 170 (see FIGS. 12 and 25), collet element 470 is rotated, thus securing locking plug 170 (steps 724 and 726). Upward torque is then applied to grip portion 414 (step 728a), thereby causing locking plug 170 to be fully inserted into implant body 110 (step 728b). Collet element 470 is rotated in reverse (step 730a), thereby releasing locking plug 170 (step 730b). Locking-plug inserter tool 400 is removed. Lastly, grasper-lock mechanism 390 is disengaged (step 732a), handles 322 and 352 are urged apart (step 732b), implant body 110 is released (step 732c), and implant-grasper tool 300 is removed.

Finally, x-rays may be taken for medical records. After checking that adequate hemostasis is maintained, the incision is closed preferably by using number 1 Vicryl in the lumbar fascia, 2-O Vicryl in the subcutaneous tissues and subcuticular 3-O Vicryl V-Loc suture for the skin. A Dermabond dressing is preferably then applied, and the patient is transferred to the post anesthetic recovery unit.

If more than one disc level is to be done during the same operation, the above procedure may be repeated.

Alternate Embodiment

A second embodiment of certain tooling is provided in FIGS. 53-77 in accordance with principles of the present invention. These second embodiments are used with implant body 110, fixation-pin assemblies 130 and 150, implant-sizing tool 200, bone-punch tool 500, and pin-inserter tool 600.

Turning to FIGS. 53-59, a second embodiment 800 of an implant-grasper tool is provided in accordance with the present invention. Implant-grasper tool 800 comprises: first element 820 pivotally connected to second element 850 by fastener 802; horn 806; and grasper portion 814. Components of implant-grasper tool 800 are preferably fabricated from AISI 314L stainless steel.

First element 820 comprises handle 822, handle linkage 824, fastener opening 826, lock-mechanism opening 828 (optional), and lower portion 830. Horn protrusion 832 is formed at the medial end of lower portion 830 and is connected to grasper linkage 834. Grasper detent 836 is formed at the distal end of grasper linkage 834. Grasper plate 838 is connected to the distal end of grasper linkage 834 as shown and has grasper flange 840. Grasper pins 842 are formed on one side of grasper plate 838 and are configured to mate with grasper-pin openings 178 on implant body 110 (see FIG. 4).

Second element 850 comprises handle 852, handle linkage 854, fastener opening 856, and lower portion 860. Horn protrusion 862 is formed at the medial end of lower portion 860 and is connected to grasper linkage 864. Grasper plate 868 is connected to the distal end of grasper linkage 864 as shown and has grasper flange 870. Grasper pins 872 are formed on one side of grasper plate 868 and are configured to mate with grasper-pin openings 178 on implant body 110 (see FIG. 4). First grasper bar 876 is connected to the lower portion of grasper linkage 864 and grasper plate 868 as shown. Second grasper bar 878 is connected to grasper plate 868 and grasper flange 870 as shown. Grasper bars 876 and 878 protrude in parallel towards grasper plate 868 when implant-grasper tool 800 is in the closed position (see FIG. 53).

Optional, locking mechanism 890 is connected to first element 820 at opening 828 by fastener 804 and is used to secure implant-grasper tool 800 in the closed position. Locking mechanism 890 comprises upper portion 892, lateral portion 894, and locking portion 896. Fastener opening 898 is formed in lateral portion 894. In yet other embodiments, locking mechanism may be connected to second element 850 instead of first element 820. Alternatively, other means for locking implant-grasper tool 800 in the closed position may be used.

Figure 60:
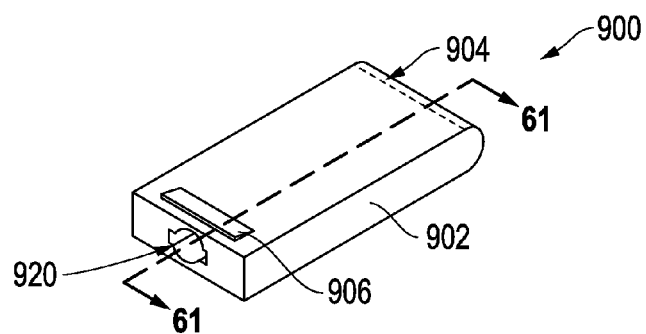
FIG. 60 depicts an isometric view of the second embodiment of a locking plug for use in combination with the second embodiment of the implant-grasper tool of FIGS. 53-59 and a second embodiment of a locking-plug inserter tool (see FIGS. 63-69).
Figure 61:
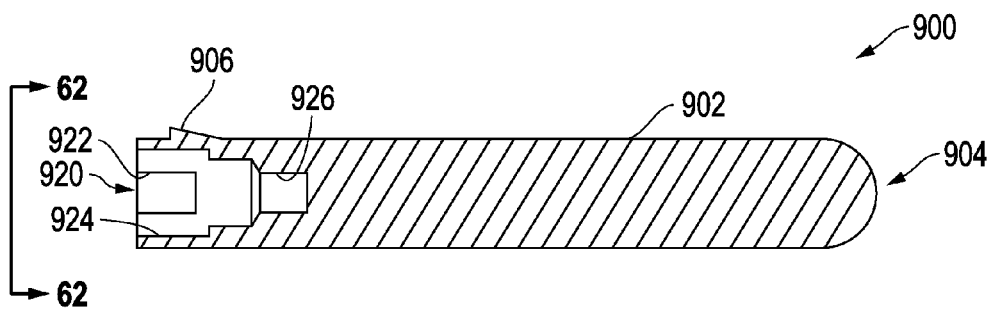
FIG. 61 depicts a cross-sectional view of the locking plug of FIG. 60 taken along section line 61-61.
Figure 62:
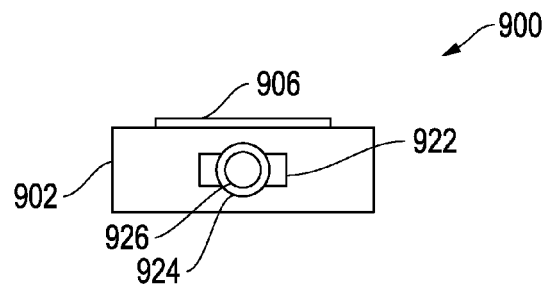
FIG. 62 depicts a side view of the locking plug of FIG. 60 taken along view 62-62.
Figure 63:
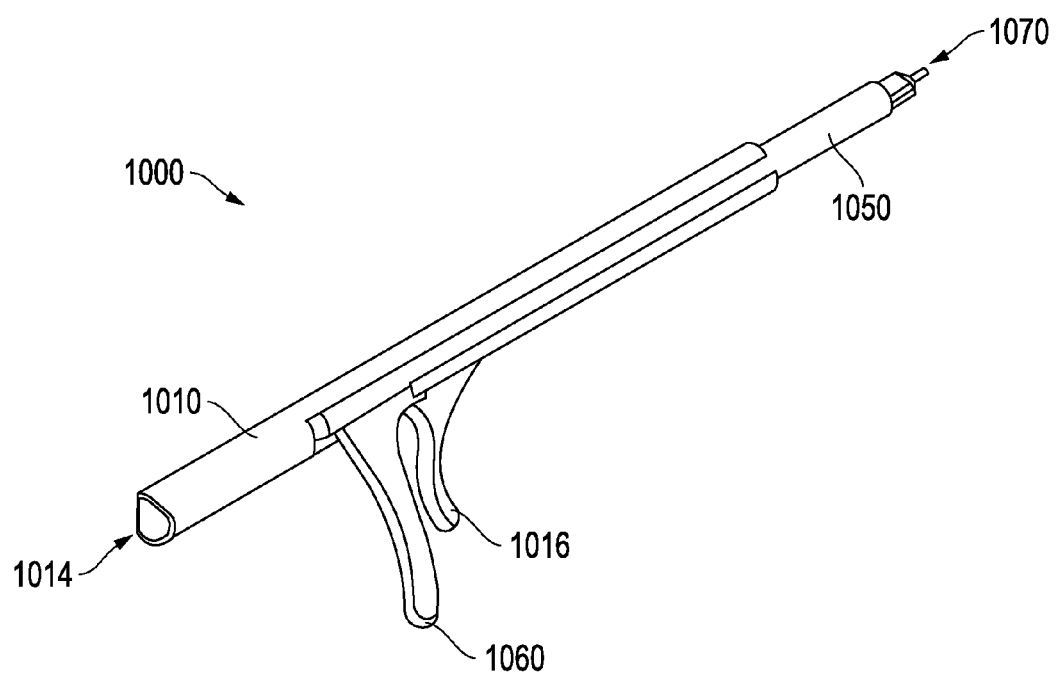
FIG. 63 depicts an isometric view of the second embodiment of a locking-plug inserter tool for use in combination with the implant-grasper tool of FIGS. 53-59 and the locking plug of FIGS. 60-62.
Figure 64:
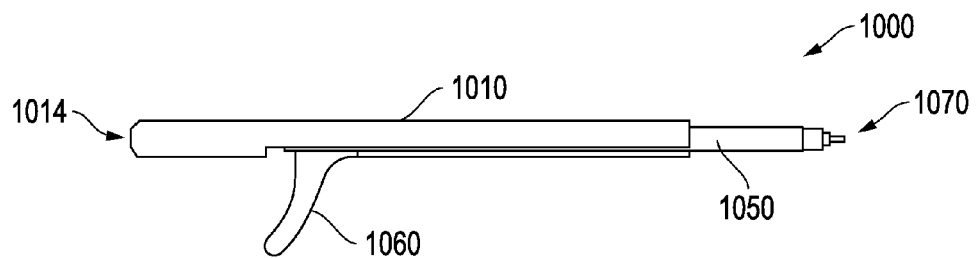
FIGS. 64-66 depict side views of the locking-plug inserter tool of FIG. 63.
Figure 65:
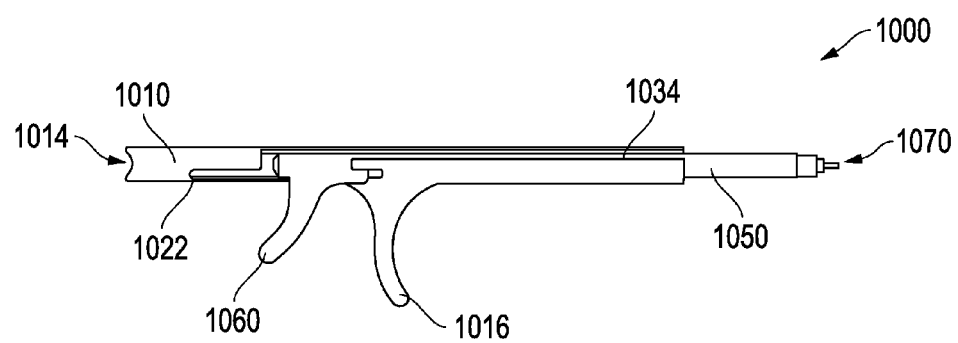

Referring to FIGS. 60-62, a second embodiment 900 of a locking plug in accordance with the present invention is provided. Locking plug 900 comprises plug body 902 having rounded-insertion surface 904. Catch 906 is formed on one surface of plug body 902. Grasper opening 920 is provided in plug body 902 in the side opposite rounded-insertion surface 904. A rectangular, alignment slot 922 is provided in grasper opening 920. A threaded, extraction slot 924 is also provided as shown. Optionally, guide channel 926 is also provided. Grasper opening 920 is configured for receiving tip 1070 of locking-plug inserter 1000 (shown in FIGS. 63-69) and also threaded tip 1184 of extractor nut 1180 (shown in FIG. 77). In other embodiments, a nonthreaded extraction slot is provided, which may be used with a self-tapping extraction nut. Preferably, locking plug 900 is 2 mm wide, 13 mm deep, and 6 mm high (for use with a 14 mm height implant body) or 8 mm high (for use with a 16 mm height implant body). Locking plug 900 is preferably fabricated from polyetheretherketone (PEEK).

Referring to FIGS. 63-69, a second embodiment 1000 of a locking-plug inserter tool is provided. Locking-plug inserter tool 1000 comprises inserter housing 1010 in slidable engagement with inserter plunger 1050. Components of locking-plug inserter 1000 are preferably fabricated from AISI 314L stainless steel.

Figure 66:
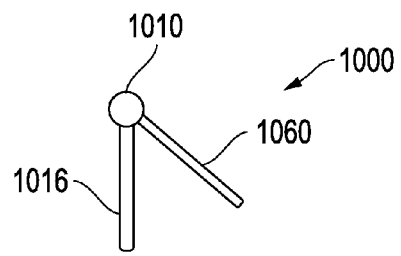
Figure 67:
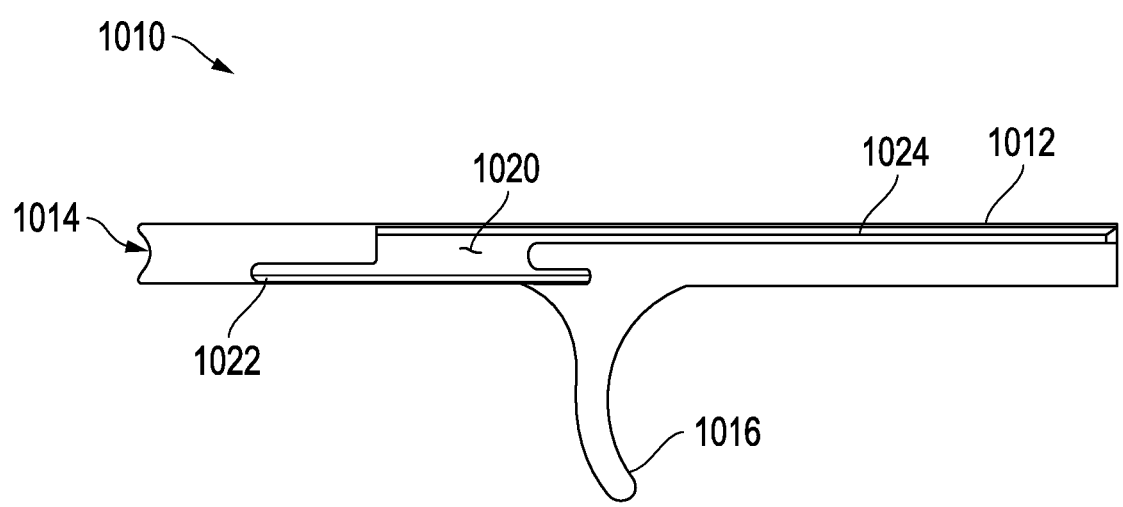
FIG. 67 depicts a side view of an inserter housing of the locking-plug inserter tool of FIG. 63.
Figure 68:
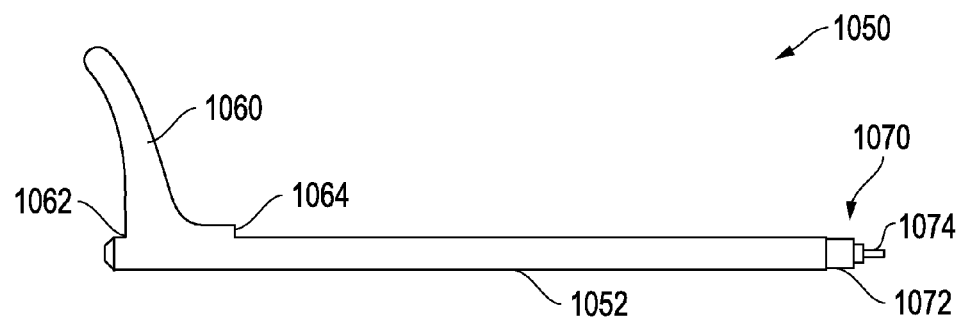
FIGS. 68-69 depict side views of an inserter plunger of the locking-plug inserter tool of FIG. 63.
Figure 69:
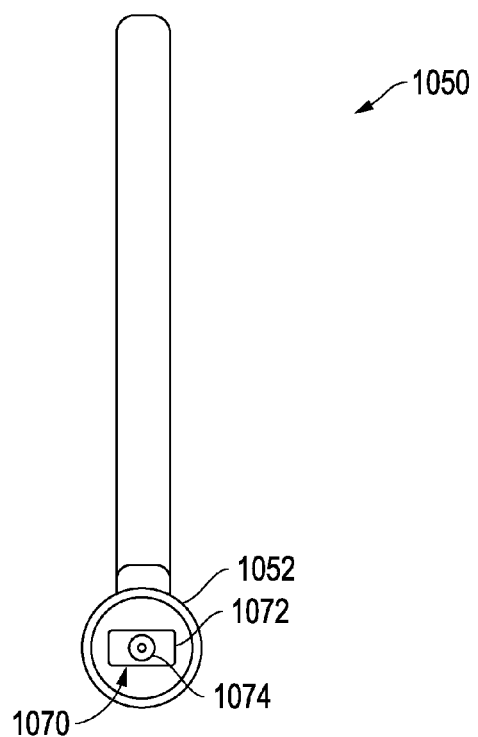
Figure 70:
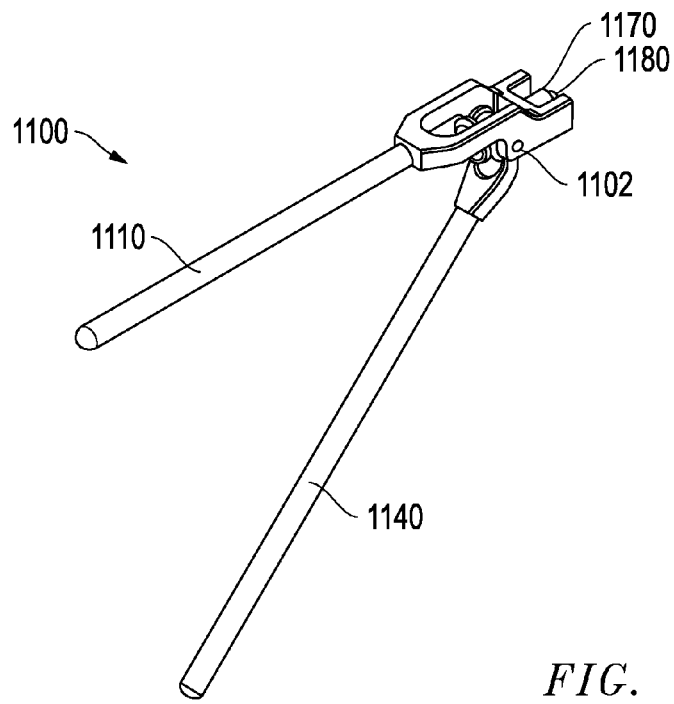
FIG. 70 depicts an isometric view of a locking-plug extractor tool for use in combination with the second embodiment of the locking plug of FIGS. 60-62.
Figure 79:
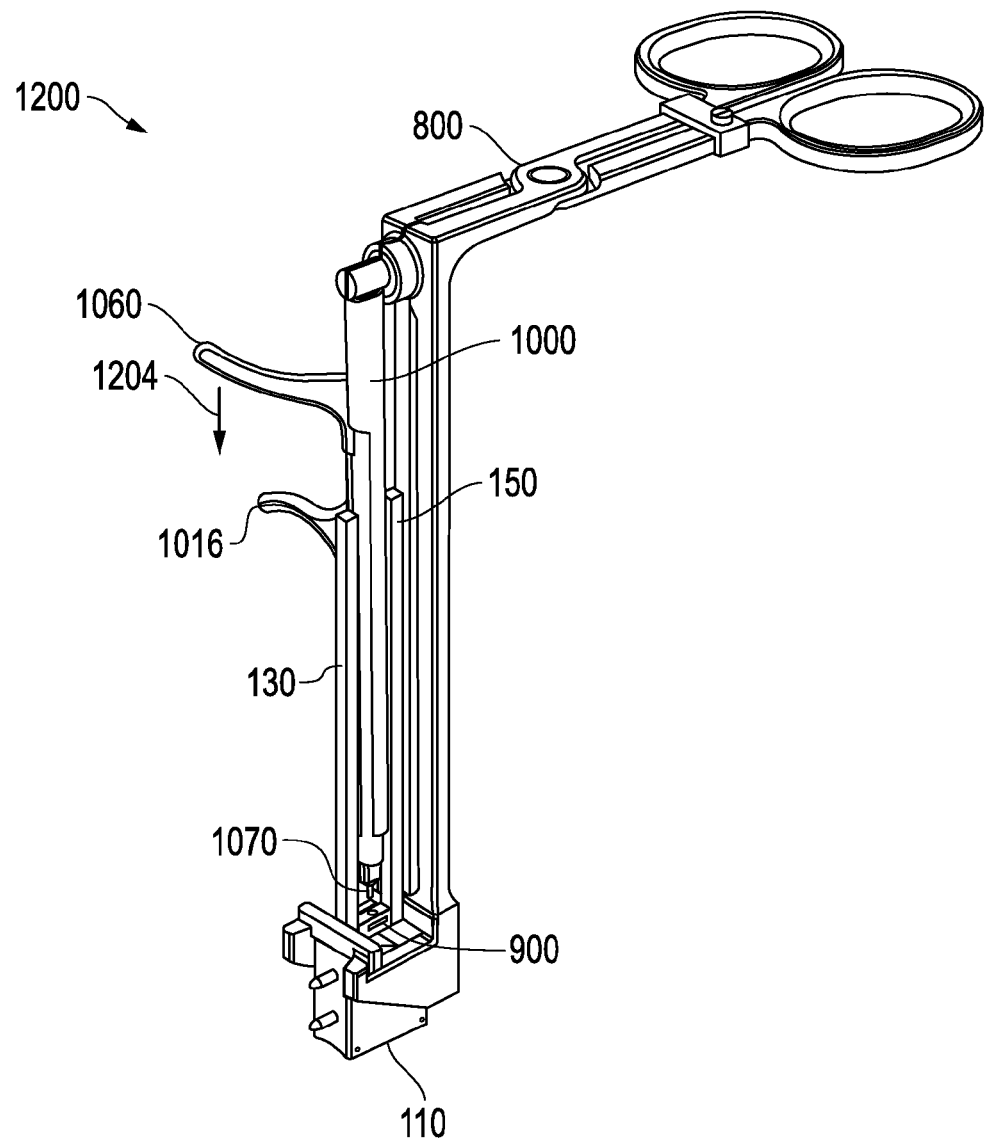
Figure 80:
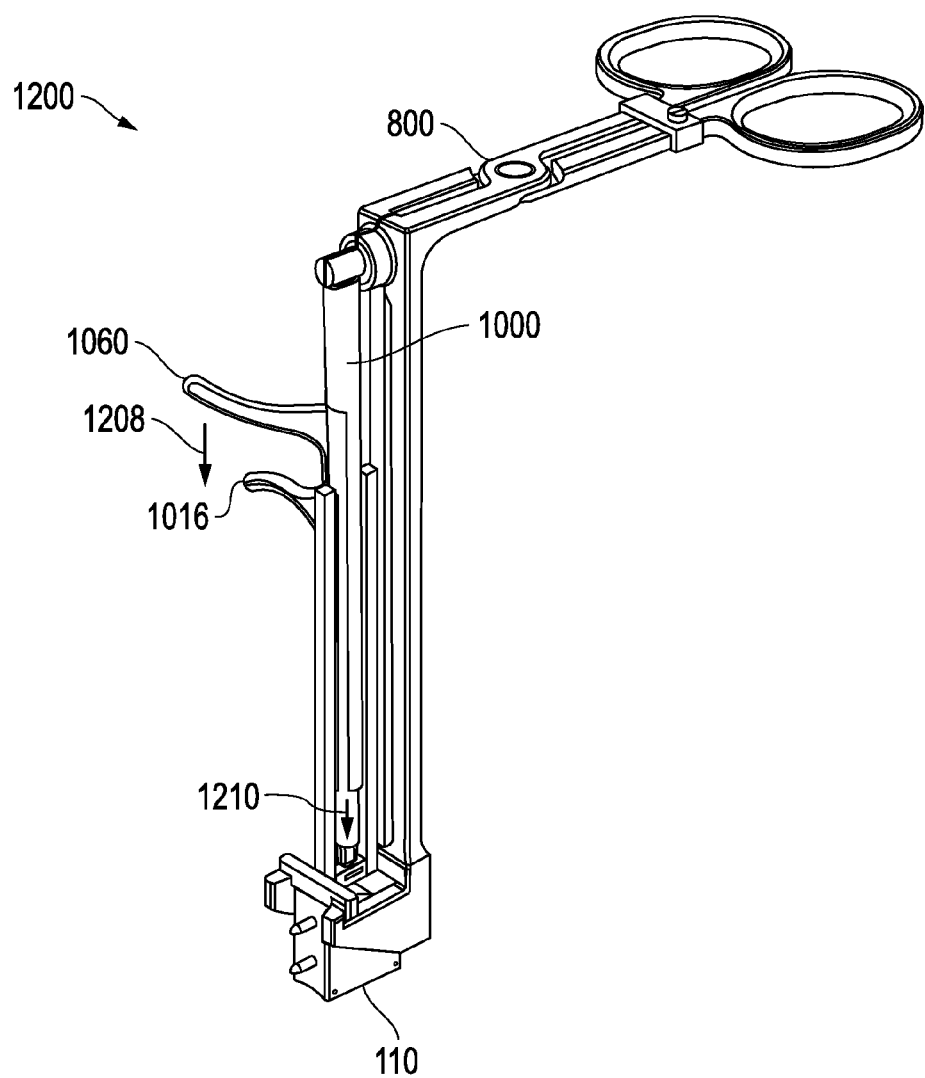
Figure 81:
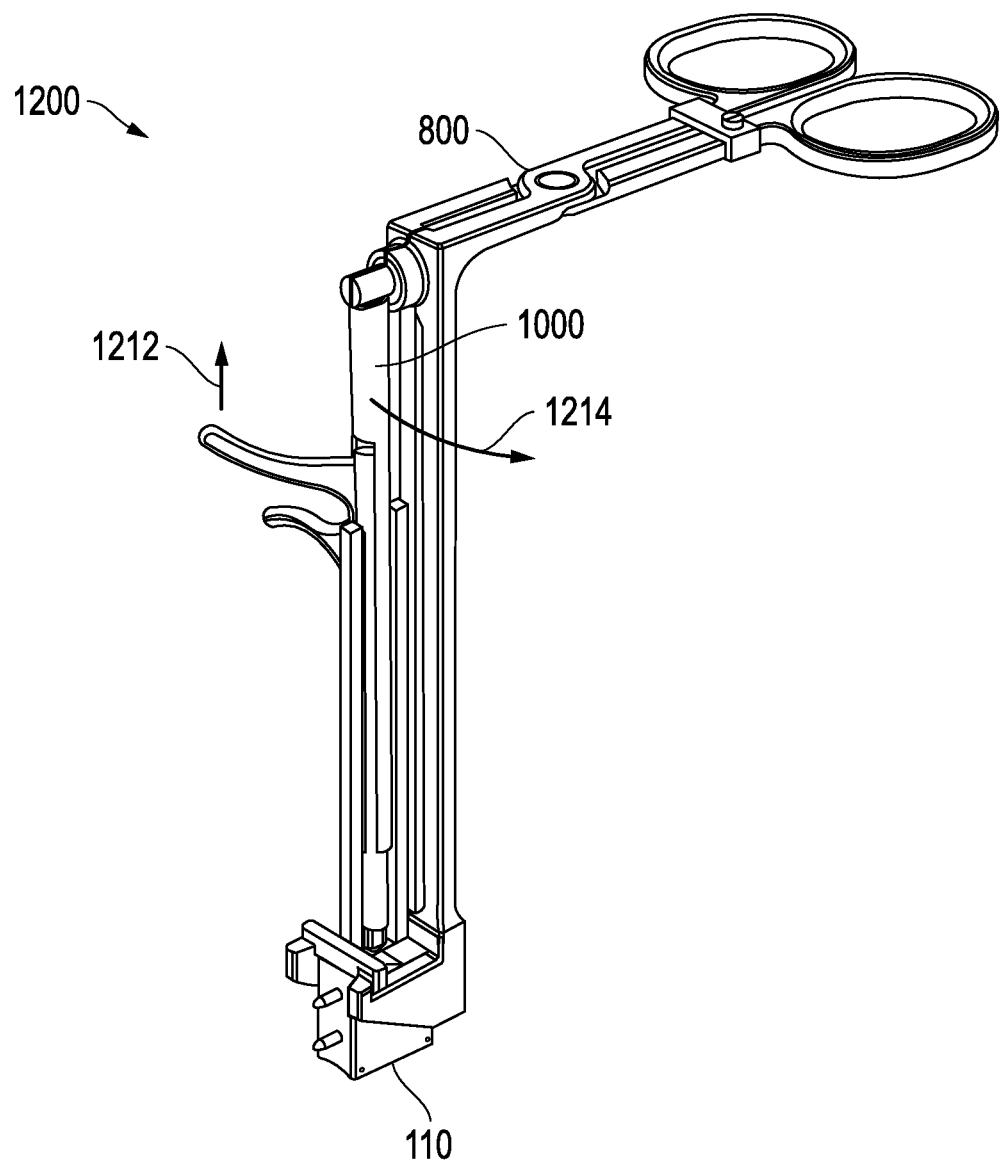

Inserter housing 1010 comprises body 1012. Body 1012 is generally cylindrical having hollow interior 1020 configured for housing body 1052 of inserter plunger 1050 (see FIG. 68). Seat 1014, preferably concave, is provided at a first end of body 1012 and is configured for mating with horn 806 of inserter-grasper tool 800 (see FIG. 79). Assembly channel 1024 is provided in the end distal to seat 1014 and is configured for allowing trigger 1060 of inserter plunger 1050 (see FIG. 68) to slide through when plunger 1050 is inserted into body 1012 to fully assemble locking-plug inserter 1000. Plug-insertion channel 1022 is provided in body 1012 and is configured to provide sufficient travel, preferably 11 mm, for inserter plunger 1050 to fully insert locking plug 900 into implant body 110 during implantation as discussed below. Trigger 1016 is provided and is circumferentially offset from plug-insertion channel 1022 as shown in FIG. 66.

Inserter plunger 1050 comprises body 1052, trigger 1060, and inserter tip 1070. Stops 1062 and 1064 are provided and are configured for engagement with ends of plug-insertion channel 1022 and are configured to allow passage through assembly channel 1024 during assembly of locking-plug inserter 1000. Alignment portion 1072 of inserter tip 1070 is provided and is configured for aligned engagement with alignment slot 922 of locking plug 900. Guide portion 1074 of inserter tip 1070 is provided and is configured for engagement with guide channel 926 of locking plug 900.

Referring to FIGS. 70-77, locking-plug extractor tool 1100 is provided. Locking-plug extractor tool 1100 comprises: extractor body 1110, extractor cam 1140, bobbin 1170, and extractor nut 1180. Extractor body 1110 is pivotally connected to extractor cam 1140. Extractor nut 1180 is concentrically within bobbin 1170, and both are in a camming relationship with extractor cam 1140. Components of locking-plug extractor 1100 are preferably fabricated from AISI 314L stainless steel.

Figure 71:
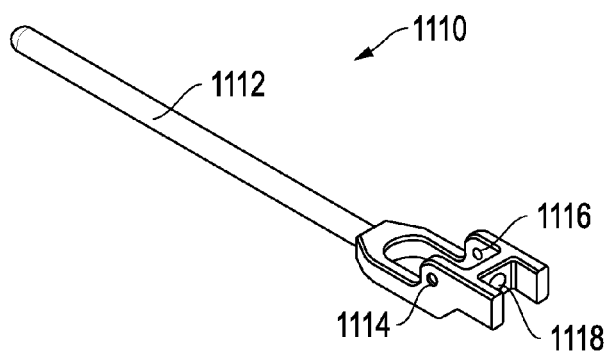
FIG. 71 depicts an isometric view of an extractor body of the locking-plug extractor tool of FIG. 70.
Figure 72:
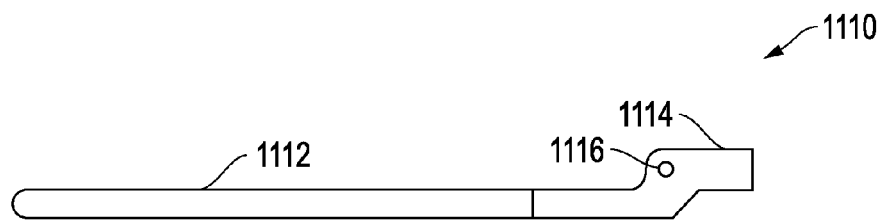
FIGS. 72-73 depict side views of the extractor body of FIG. 71.
Figure 73:
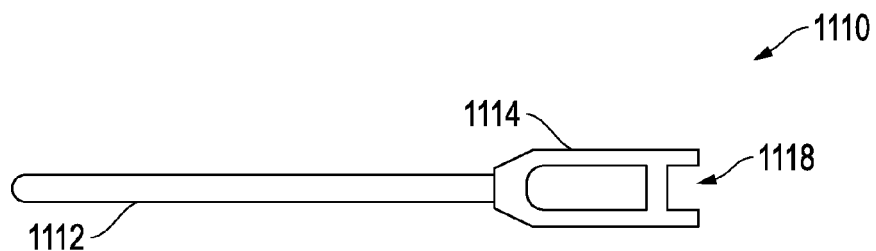

Referring more particularly to FIGS. 71-73, extractor body 1110 comprises handle 1112 and brace frame 1114. Fastener opening 1114 is provided for receiving fastener 1102. Extractor opening 1118 is provided and is configured for receiving bobbin 1170.

Figure 74:
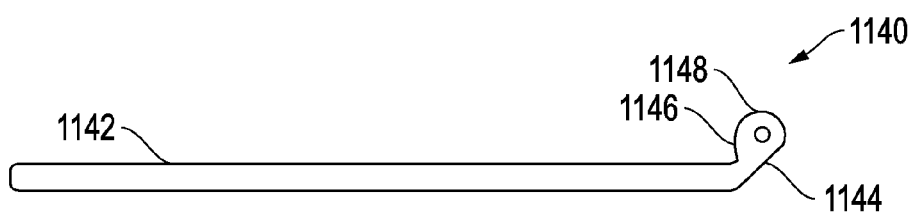
FIGS. 74-75 depict side views of an extractor cam of the locking-plug extractor tool of FIG. 70.
Figure 75:
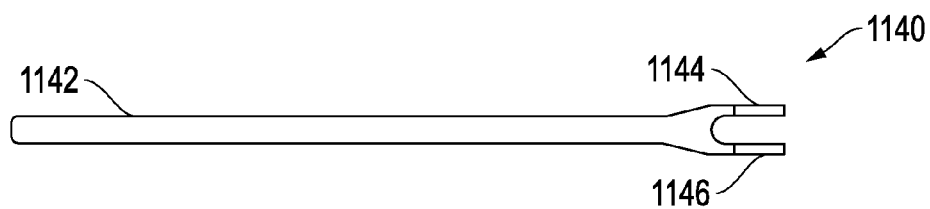

Referring more particularly to FIGS. 74-75, extractor cam 1140 comprises handle 1142 and cam head 1144. Camming surface 1146 is provided on cam head 1144. Fastener opening 1148 is provided for receiving fastener 1102.

Figure 76:
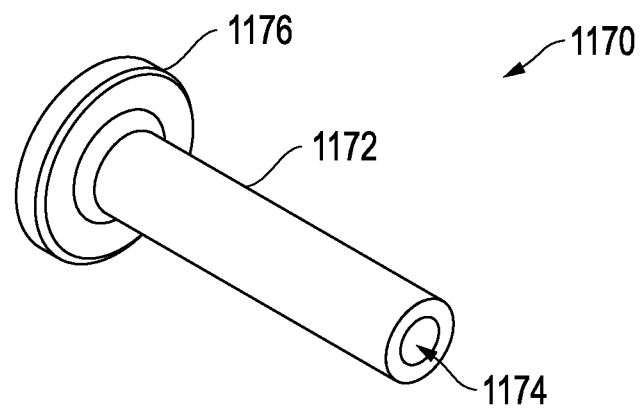
FIG. 76 depicts an isometric view of a bobbin of the locking-plug extractor tool of FIG. 70.

Referring more particularly to FIG. 76, bobbin 1170 is provided. Bobbin 1170 comprises cylindrical body 1172 having hollow interior 1174. Hollow interior 1174 is configured for receiving body 1182 of extractor nut 1180 (see FIG. 77). Bobbin head 1176 is also provided and is configured for engagement with camming surface 1146 of extractor cam 1140 and also is configured for engagement with extractor-nut head 1186 of extractor nut 1180.

Figure 77:
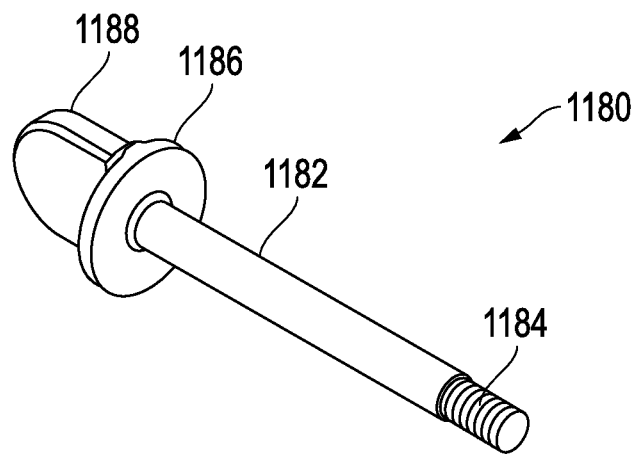
FIG. 77 depicts an isometric view of an extractor nut of the locking-plug extractor tool of FIG. 70.

Referring more particularly to FIG. 77, extractor nut 1180 is provided. Extractor nut 1180 comprises cylindrical body 1182 having threaded tip 1184. Threaded tip 1184 is configured for engaging extraction slot 924 of locking plug 900 (see FIG. 61). Extractor-nut head 1186 is configured for engagement with bobbin head 1176 of bobbin 1170.

Method of Implantation Using Second Embodiment

Referring to FIGS. 78-81, a preferred method 1200 of implanting ILFD 100 using locking plug 900 (instead of 170) in a spine 10 (see FIG. 1) of a patient using implant-sizing tool 200 (discussed above), implant-grasper tool 800, locking-plug inserter tool 1000, bone-punch tool 500, and pin-inserter 600 is described. For clarity, spine 10 is omitted. Method 1200 is substantially the same as described above and shown in FIGS. 36-52, except as described below.

Figure 52:
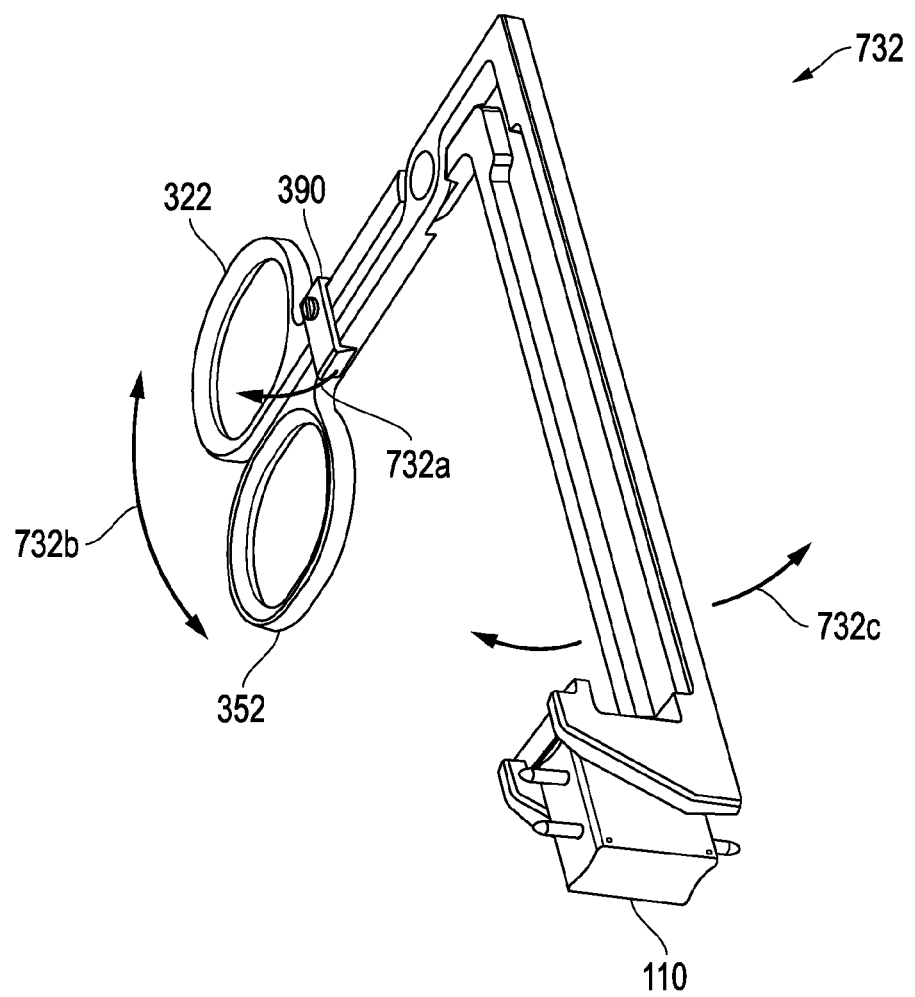
Figure 53:
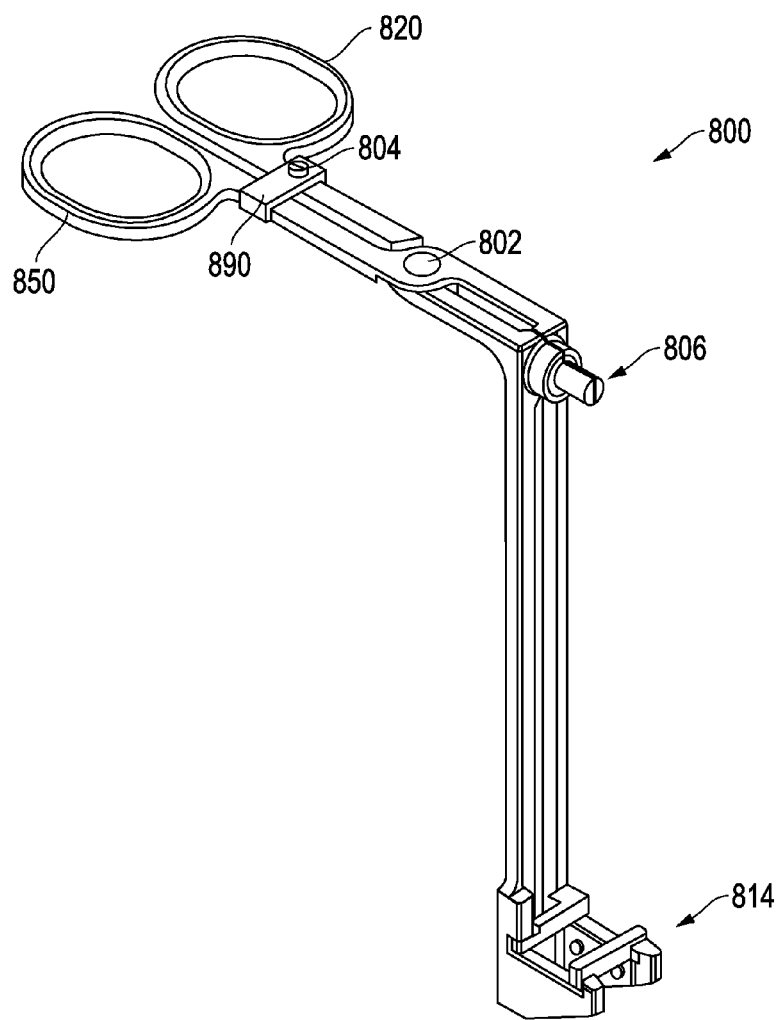
FIG. 53 depicts an isometric view of a second embodiment of an implant-grasper tool for use in combination with a second embodiment of a locking-plug inserter tool (see FIGS. 63-69) and a second embodiment of a locking plug (see FIGS. 60-62).
Figure 54:
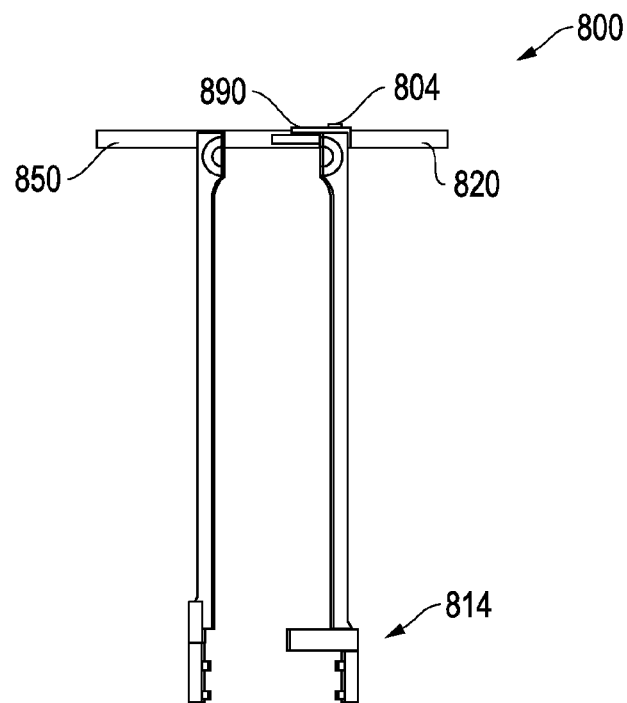
FIG. 54 depicts a side view of the implant-grasper tool of FIG. 53 exemplified in an open position.
Figure 55:
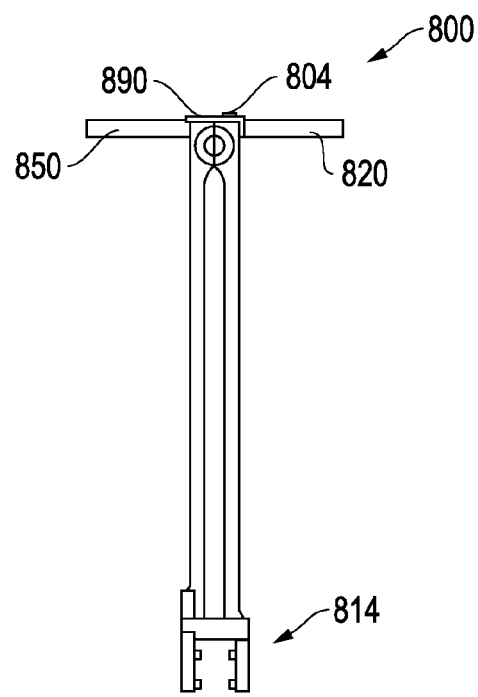
FIG. 55 depicts a side view of the implant-grasper tool of FIG. 53 exemplified in an closed position.
Figure 56:
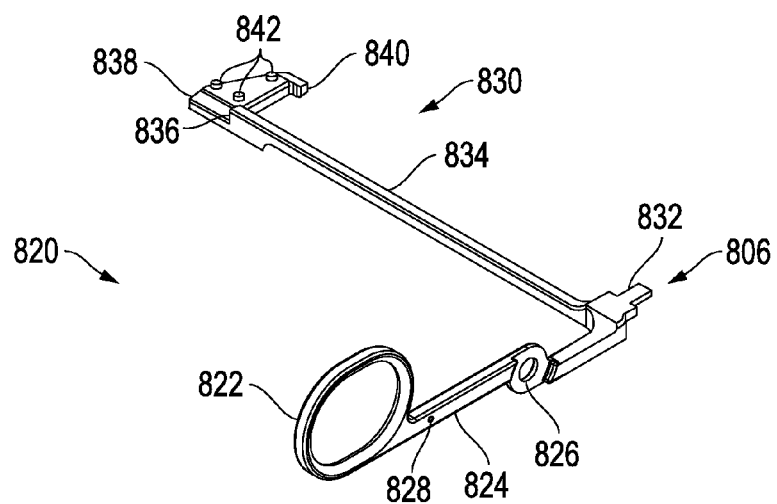
FIGS. 56-57 depict isometric views of elements of the implant-grasper tool of FIG. 53.
Figure 57:
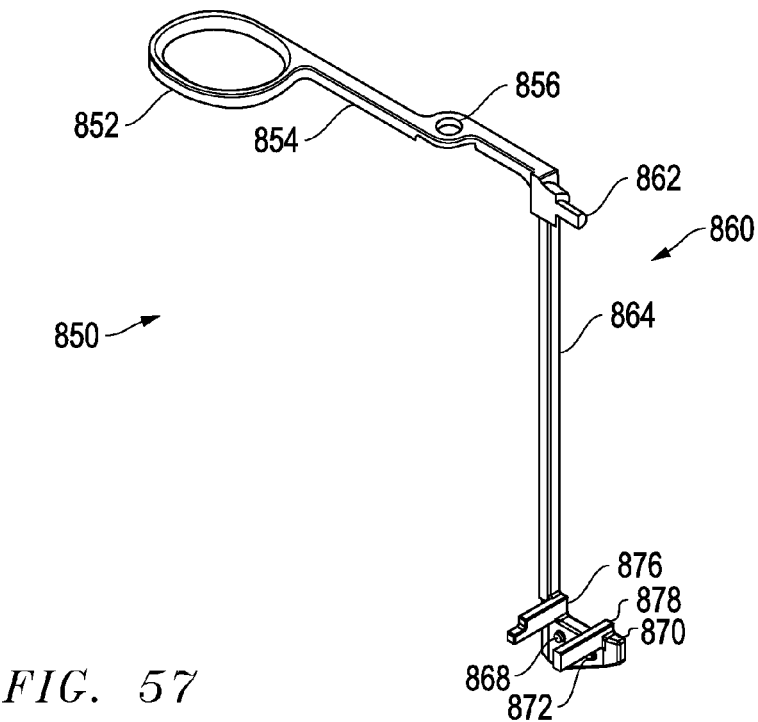
Figure 58:
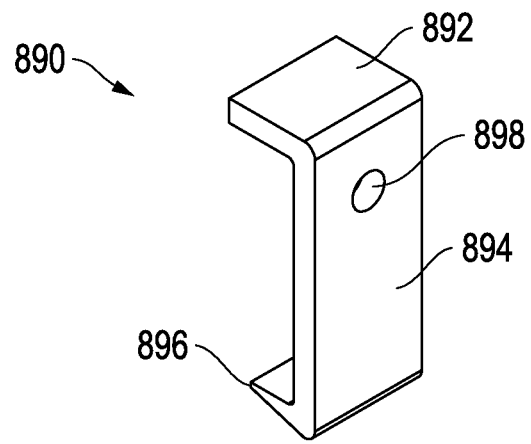
FIG. 58 depicts an isometric view of a locking mechanism of the implant-grasper tool of FIG. 53.
Figure 59:
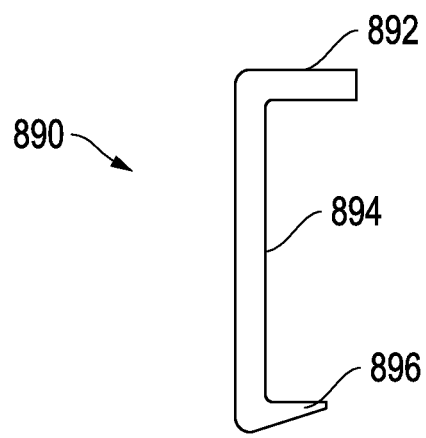
FIG. 59 depicts a side view of the locking mechanism of FIG. 58.
Figure 78:
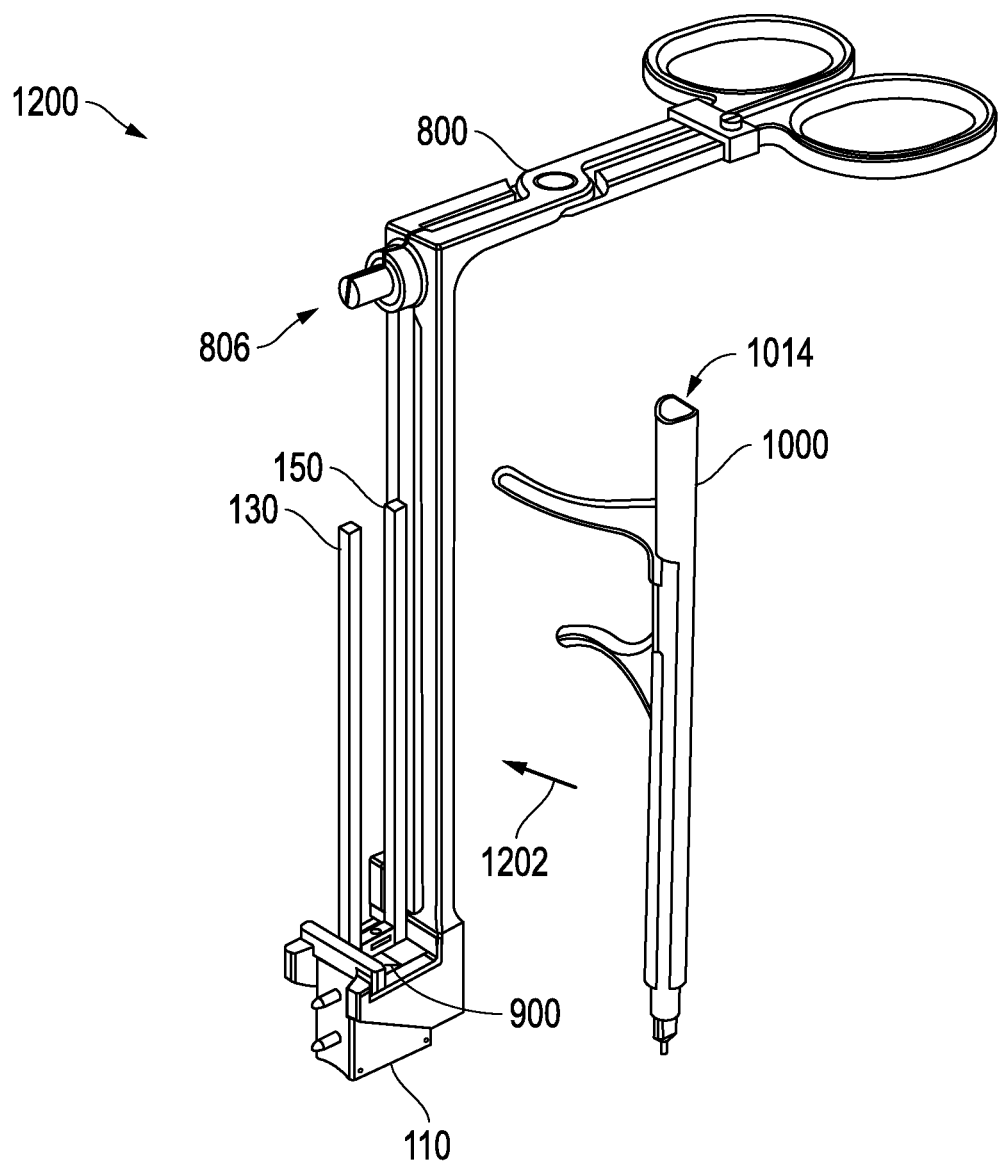
FIGS. 78-81 depict perspective views exemplifying the sequence of steps for implanting the ILFD of FIG. 2 using the second embodiments of tooling shown in FIGS. 53-69.

In method 1200, assembly and placement of implant body 110, fixation-pin assemblies 130 and 150, locking plug 900 as shown in FIG. 78, and preceding steps, are substantially the same as described above and shown in FIGS. 36-44. Next, locking-plug inserter tool 1000 is positioned so that concave seat 1014 engages horn 806 (step 1202). Trigger 1060 is then depressed until inserter tip 1070 addresses grasper opening 920 of locking plug 900 (step 1204) and then fully depressed until stop 1064 reaches the end of channel 1022, at which point locking plug 900 will be fully inserted (steps 1208 and 1210). Trigger 1060 is then raised (step 1212) and locking-plug inserter tool 1000 is removed (step 1214). Breakaway portions 132*b* and 152*b* of fixation-pin assemblies 130 and 150 may be removed now or, alternatively, have been removed after partial insertion of locking plug 900 (see FIG. 45). Lastly, implant-grasper tool 800 may be removed as shown in FIG. 52 and described above and all remaining steps may be performed.

Method of Extraction

Figure 82:
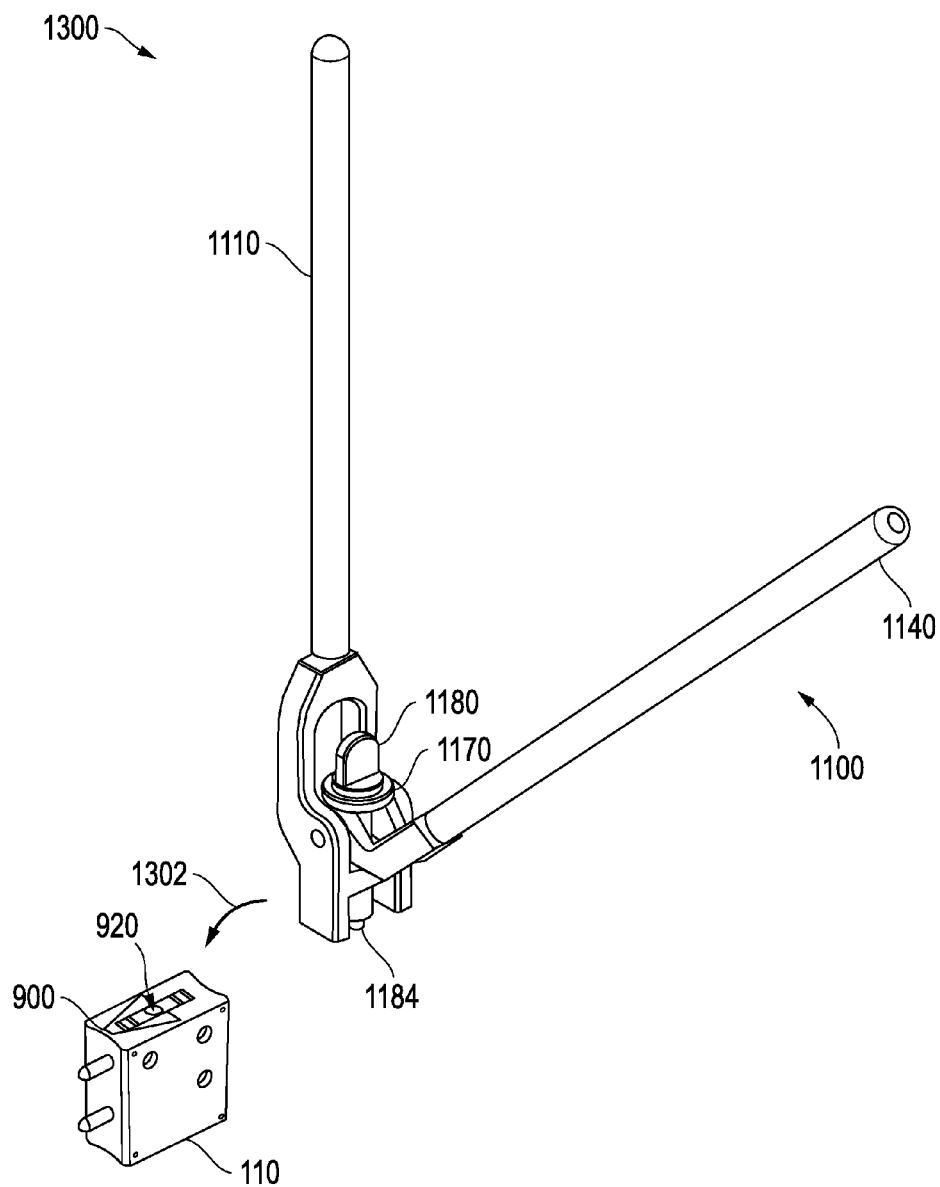
FIGS. 82-84 depict perspective views exemplifying the sequence of steps for extracting the locking plug of FIGS. 60-62 using the locking-plug extractor tool of FIGS. 78-81.
Figure 83:
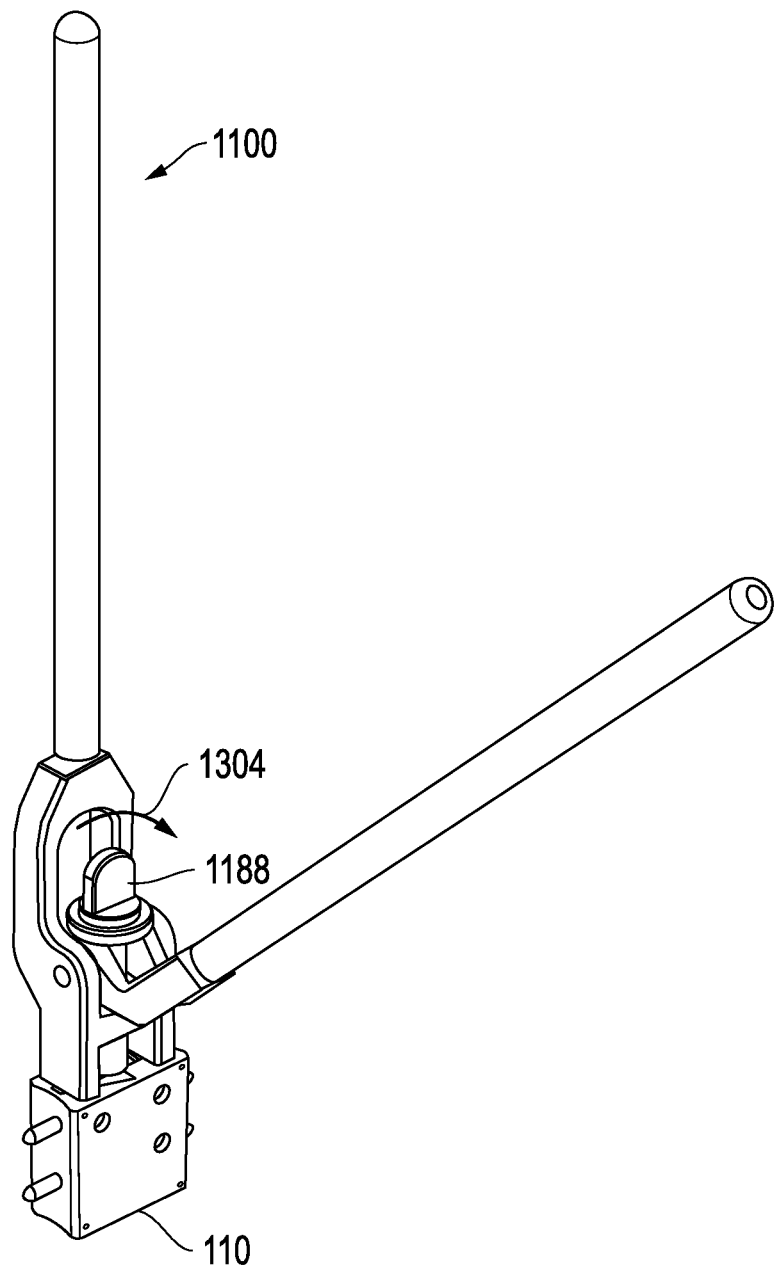
Figure 84:
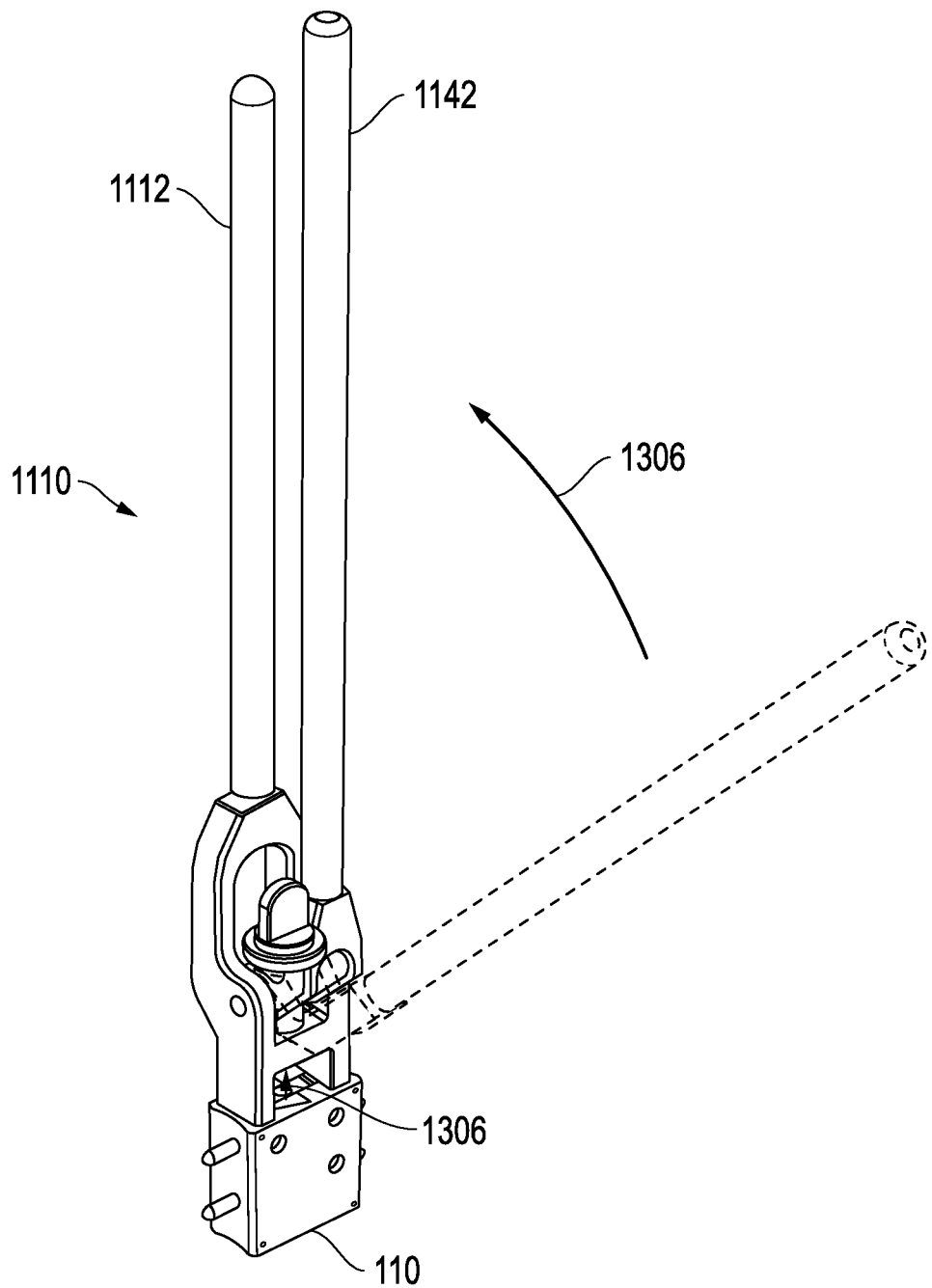

Referring to FIGS. 82-84, a preferred method 1300 of extracting locking plug 900 from implant body 110 is provided. For clarity, spine 10 is omitted. The surgical steps are substantially the same as described above.

First, locking-plug extractor tool 1100 is positioned over implant body 110 such that threaded tip 1184 of extractor nut 1180 is proximate to grasper opening 920 of locking plug 900 (step 1302). Next, wing 1188 is rotated such that threaded tip 1184 engages extraction slot 924 of grasper opening 920 (step 1304). Then, handle 1142 of extractor cam 1140 is raised (step 1306). This creates a camming action that urges bobbin 1170 upwards and extractor nut 1180 upwards, thereby partially extracting locking plug 900 from implant body 110. Lastly, locking-plug extractor tool 1100 and locking plug 900 are removed and the ILFD may be disassembled and removed.

While the aspects of the present disclosure may be susceptible to various modifications and alternative forms, specific embodiments have been shown by way of example in the drawings and have been described in detail herein. But, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A spinal implant comprising:
an implant body having at least six surfaces and a hollow interior;
the body having a dorsal surface and an opposite ventral surface;
the body having a cephalad surface and an opposite caudal surface;
the body having a left surface and an opposite right surface;
a slot formed on the dorsal surface that extends to the hollow interior;
a pair of fixation-pin openings formed on the cephalad surface and extending to the hollow interior;
a pair of fixation-pin openings formed on the caudal surface and extending to the hollow interior surface;
a cephalad fixation pin assembly having a cephalad rod and a pair of cephalad pins extending from the rod;
the cephalad rod having an embedded portion and a breakaway portion;
the cephalad fixation pin assembly insertable through the slot;
the cephalad pins insertable through the cephalad fixation-pin openings to position the breakaway portion exterior to the body;
a caudal fixation pin assembly having a caudal rod and a pair of caudal pins extending from the caudal rod;
the caudal rod having an embedded portion and a breakaway portion;
the caudal fixation pin assembly insertable through the slot;
the caudal pins being insertable through the caudal portals to position the breakaway portion exterior to the body; and,
a locking plug insertable into the hollow interior between the embedded portion of the cephalad rod and the embedded portion of the caudal rod.

2. The spinal implant of claim 1, further comprising:
the cephalad rod embedded portion and breakaway portion separated by a breakaway notch on the cephalad rod; and,
the cephalad rod embedded portion and breakaway portion separated by a breakaway notch on the caudal rod.

3. The spinal implant of claim 1, further comprising:
the cephalad pins inserted through the cephalad fixation-pin openings positions the notch on the cephalad rod proximate to the dorsal surface; and,
the caudal pins inserted through the caudal fixation-pin openings positions the notch on the caudal rod proximate to the dorsal surface.

4. The spinal implant of claim 1, further comprising:
the fixation cephalad pins and caudal pins have tips that are ogival shaped.

5. The spinal implant of claim 1, further comprising:
the rod has a 2 mm×2 mm square cross section.

6. The spinal implant of claim 1, further comprising:
the rod and fixation pins are fabricated from Tivanium.

7. The spinal implant of claim 1, further comprising:
the dorsal surface and ventral surface being recessed inwards.

8. The spinal implant of claim 1, further comprising:
an orientation indicator on the body to indicate visually proper orientation during an implantation.

9. The spinal implant of claim 1, further comprising:
a plurality of notches on the left surface of the body; and,
a plurality of matching notches on the right side of the body.

10. The spinal implant of claim 1, further comprising:
the body has a depth extending from the dorsal surface to the ventral surface of approximately 16 mm; and,
the body has a width extending from the left surface to the right surface of approximately 8 mm.

11. The spinal implant of claim 1, further comprising:
the body is preferably fabricated from polyetheretherketone (PEEK).

12. The spinal implant of claim 1, further comprising:
the slot is configured to receive the cephalad fixation-pin assembly, the caudal fixation-pin assembly, and the locking plug.

13. The spinal implant of claim 1, further comprising:
placement-detection rods are located on the body between the left surface and the right surface.

14. The spinal implant of claim 1, further comprising:
placement-detection rods are made of tantalum rods or titanium or other radiologically detectable material.

15. The spinal implant of claim 1, further comprising:
a recess formed in the slot;
the locking plug having:
a rounded-insertion surface; and,
a catch formed for engaging the recess in the slot when the locking pin is fully inserted into the slot.

16. The spinal implant of claim 1, further comprising:
the locking plug having:
a grasper-pin opening provided on a side of the locking plug opposite to the rounded-insertion surface.

17. An inserter tool for inserting the spinal implant of claim 1, comprising:
a pair of handle elements pivotally coupled to one another, each of the handle elements comprising:
an upper portion, and,
a lower portion perpendicular to the upper portion;
an implant grasper formed by the lower portions of the handle elements;
a handle formed by the upper portions; and, a locking mechanism for locking the handle and implant grasper in a locked position.

18. A bone-punch tool engageable with the spinal implant of claim 1, comprising:
  a first handle element comprising a first handle portion and a first lower portion perpendicular to the handle portion;
  a second handle element comprising a second handle portion and a second lower portion perpendicular to the handle portion;
  the first handle element pivotally connected to the second handle element such that the lower portions are urged apart when the handle portions are urged apart; and,
  a pair of pins coupled to the first lower portion and extending perpendicularly outward from the first lower portion.

19. An implant-grasper tool for securing to the spinal implant of claim 1, comprising:
  a first handle element comprising a first handle portion and a first lower portion perpendicular to the handle portion;
  a second handle element comprising a second handle portion and a second lower portion perpendicular to the handle portion;
  the first handle element pivotally connected to the second handle element such that the lower portions are urged apart when the handle portions are urged apart;
  an implant grasper is formed by the lower portions of the first and second handle elements and is configured for grasping an interlaminar fixation device.

20. A locking-plug inserter tool for inserting a locking plug into the spinal implant of claim 1, comprising:
  a plunger comprising:
    a connection end, and,
    a means for detachably securing a locking plug; and,
  a handle element comprising:
    a grip,
    a fulcrum-slot configured for insertion into a inserter tool and for providing a fulcrum for depressing the plunger, and,
    a connection end pivotally connected to the connection end of the plunger.

21. A locking-plug inserter tool for inserting a locking plug into the spinal implant of claim 1, comprising:
  an inserter-plunger element comprising:
    an elongated plunger body,
    a plunger trigger protruding outward from the plunger body, and
    a inserter tip at one end of the plunger body configured for mating with an opening on a locking plug; and
  a housing comprising:
    a hollow interior configured for housing the plunger body in a slidable relation,
    a seat at a first end of the housing,
    an open end at a second end of the housing distal the first end,
    an assembly channel configured to permit passage of the plunger trigger during assembly of the locking-plug inserter tool,
    a guide channel configured to permit a predetermined amount slidable travel of the inserter-plunger when the locking-plug inserter tool is assembled, and
    a trigger protruding outward from the housing.

22. A locking-plug extractor tool for removing a locking plug from the spinal implant of claim 1, comprising:
  an extractor nut comprising:
    a cylindrical body having a first and a second end,
    a threaded tip at the first end of the body, and
    an enlarged head coupled to the second end of the body,
    a wing capable of manual rotation of the extractor nut coupled to the head;
  an extractor cam comprising:
    a handle, and
    a cam head coupled to the handle;
  an extractor body comprising:
    a handle,
    a frame coupled to the handle,
    an opening in the frame configured for receiving the extractor nut and permit slidable movement of the extractor nut;
  the extractor cam being pivotally fastened to the extractor body,
  wherein the extractor cam urges the extractor nut when the extract cam is pivoted relative to the extractor body.

* * * * *